US011532107B2

(12) United States Patent
Chappell et al.

(10) Patent No.: US 11,532,107 B2
(45) Date of Patent: Dec. 20, 2022

(54) METHODS AND SYSTEMS OF MULTIPHASE ARTERIAL SPIN LABELING

(71) Applicant: Oxford University Innovation Limited, Oxford (GB)

(72) Inventors: Michael Chappell, Oxford (GB); Martin Craig, Oxford (GB); James Larkin, Oxford (GB); Manon Simard, Oxford (GB)

(73) Assignee: OXFORD UNIVERSITY INNOVATION LIMITED, Oxford (GB)

(*) Notice: Subject to any disclaimer, the term of this patent is extended or adjusted under 35 U.S.C. 154(b) by 931 days.

(21) Appl. No.: 16/171,682

(22) Filed: Oct. 26, 2018

(65) Prior Publication Data
US 2019/0130609 A1    May 2, 2019

Related U.S. Application Data

(60) Provisional application No. 62/577,994, filed on Oct. 27, 2017.

(51) Int. Cl.
| A61B 5/00 | (2006.01) |
| G06T 11/00 | (2006.01) |
| G06T 7/00 | (2017.01) |
| G06K 9/62 | (2022.01) |
| A61B 5/026 | (2006.01) |
| G01R 33/56 | (2006.01) |
| G01R 33/563 | (2006.01) |
| G01R 33/565 | (2006.01) |
| G01R 33/561 | (2006.01) |
| G01R 33/483 | (2006.01) |

(52) U.S. Cl.
CPC .......... G06T 11/008 (2013.01); A61B 5/0042 (2013.01); A61B 5/0263 (2013.01); A61B 5/7485 (2013.01); G01R 33/5601 (2013.01); *G01R 33/565* (2013.01); *G01R 33/56366* (2013.01); *G06K 9/6223* (2013.01); *G06T 7/0012* (2013.01); *G06T 11/005* (2013.01); *A61B 2576/026* (2013.01); *G01R 33/4835* (2013.01); *G01R 33/5608* (2013.01); *G01R 33/5616* (2013.01); *G06T 2207/10088* (2013.01); *G06T 2207/20182* (2013.01); *G06T 2207/30016* (2013.01); *G06T 2207/30104* (2013.01); *G06T 2211/404* (2013.01); *G06T 2211/436* (2013.01)

(58) Field of Classification Search
CPC ............ A61B 2576/026; A61B 5/0042; A61B 5/0263; A61B 5/7485; G01R 33/4835; G01R 33/5601; G01R 33/5608; G01R 33/5616; G01R 33/56366; G01R 33/565; G06T 11/005; G06T 11/008; G06T 11/60; G06T 2207/10088; G06T 2207/20182; G06T 2207/30016; G06T 2207/30104; G06T 2211/404; G06T 2211/436; G06T 7/0012
See application file for complete search history.

(56) References Cited

U.S. PATENT DOCUMENTS

2010/0240983 A1* 9/2010 Jung ................ A61B 5/055
600/410
2013/0253895 A1* 9/2013 Okell ................ A61B 6/507
703/11

* cited by examiner

*Primary Examiner* — Christopher L Cook
(74) *Attorney, Agent, or Firm* — Thomas|Horstemeyer, LLP

(57) ABSTRACT

The present disclosure is directed to systems and methods of multiphase pseudo-continuous arterial spin labeling.

21 Claims, 16 Drawing Sheets

METHODS AND SYSTEMS OF MULTIPHASE ARTERIAL SPIN LABELING

CROSS-REFERENCE TO RELATED APPLICATION

This application claims the benefit of and priority to U.S. Provisional Patent Application No. 62/577,994 filed Oct. 27, 2017, which is entirely incorporated herein by reference.

TECHNICAL FIELD

The present disclosure generally relates to medical imaging and, more particularly, relates to systems and methods for providing clinicians with blood flow and tissue perfusion information to help make diagnostic, prognostic and/or therapeutic decisions.

BACKGROUND

Diseases that affect the blood supply to the brain are leading causes of death and disability. Medical imaging techniques that visualize blood flow to the brain are important for accurate diagnosis, prognosis, and treatment decision-making. Currently, many common methods for assessing blood flow through the arteries or tissue perfusion rely on injecting an exogenous contrast agent. Use of exogenous contrast agents is invasive, increases the scan set-up time, decreases patient comfort, and excludes some patients with contraindications to contrast agents. For example, Gadolinium-based contrast agents can be problematic when used in patients with kidney dysfunction. Many methods also use ionizing radiation, with its associated risks, which limits the number of scans that each patient can undergo.

These needs have prompted the growth of arterial spin labeling (ASL), a magnetic resonance imaging (MRI) based method that uses blood water as an endogenous tracer. ASL is an MRI method that can generate angiograms and tissue perfusion maps without ionizing radiation or contrast agents. Typically ASL is used to generate maps of blood flow at the tissue level (perfusion), which can be used for identifying brain regions that are at risk of permanent damage due to compromised blood supply.

It is now widely accepted that pseudo-continuous labelling is the preferred scheme for ASL perfusion imaging due to superior signal-to-noise ratio (SNR) over pulsed variants. A short-coming of PCASL, however, is sensitivity to phase mismatch due to the presence of off-resonance fields, and blood flow velocity in the labelling plane; this can lead to inefficient labelling, resulting, in the worst case, in the loss of perfusion information in a whole perfusion territory fed, or at least variations in labelling efficiency for blood destined for different regions of the brain, not routinely accounted for in quantification methods. Accordingly, there is a need to correct the aforementioned deficiencies and inadequacies.

SUMMARY

The present disclosure provides various solutions to overcome the aforementioned deficiencies and inadequacies. In an embodiment, the present disclosure is particularly applicable to multi-phase PCASL (MP PCASL), described in more detail below, providing an improvement over conventional multi-phase PCASL. In an embodiment, the present disclosure addresses and provides a solution to the problem of phase mismatch that occurs in conventional multi-phase PCASL.

The 'standard' or conventional multi-phase PCASL approach is one of fitting a model to the multi-phase data. An example of the conventional approach is described in the paper by Jung et al. [13]. This approach, however, is inaccurate for the parameters sought in the face of noise. There is an established effect of bias in some estimated parameters due to noise, and insufficient SNR in typical data to reliably estimate other parameters of interest [17]. Up until now, this problem has not been recognized in the context presented herein.

The present disclosure solves the problem due the established effect of bias. In an embodiment, after placing a subject in association with an MRI scanner, multi-phase PCASL data is obtained. After the multi-phase PCASL data is obtained, first, a biased fit of the data is made. Next, to exploit features of the data, a clustering approach is applied to the data to identify the one or more regions of voxels of interest ("ROI's") of the subject having one or more selected common properties. Regions of voxels can be grouped or clustered based on a commonality of the one or more parameters, such as phase parameters. The one or more ROI's can be averaged, by for example averaging individual timecourses of data in the separate voxels within a grouping. The averaging of the individual timecourses can produce a grouping having higher quality, less noisy data. The timecourses within a grouping can be analysed using a second model-fitting to determine or estimate the one or more parameter values common to the ROI defined by the grouping. An estimated parameter value can be an estimated phase parameter. The estimated one or more parameter values, for example an estimated phase parameter, of the ROI(s) can then be applied to a third model fitting to correct for mismatch, for example phase mismatch, within the multi-phase data originally obtained and to obtain a determination of perfusion and/or cerebral blow flow from the data.

Thus, in an embodiment, the present disclosure provides a combination of model-fitting and (voxel or supervoxel based) clustering in a series of stages that provides an accurate estimation of certain one or more parameters that would otherwise produce a biased result or be highly variable in the face of noisy ASL data. Accordingly, in various aspects, the present systems and methods provide an improvement over the conventional ASL approach, in particular the conventional multi-phase PCASL approach. They can correct for a previously unidentified bias (such as phase mismatch) that occurs in the conventional multi-phase PCASL approach. The present systems and methods also offer more information than is currently extracted from the conventional approach to provide corrections for effects that reduce the accuracy of conventional PCASL.

In various embodiments, computer implemented methods and systems for perfusion imaging are provided. In an embodiment, the method can comprise: positioning an imaging scanner in relation to a subject; setting a labeling plane within the subject in which the scanner labels blood; labeling blood of the subject in the labeling plane with the scanner with arterial spin labeling using a plurality of phase increments; acquiring a data set from the labeled blood in the subject using the imaging scanner; reconstructing raw multiphase data from the acquired data set; fitting a function to the raw multiphase data to generate a raw parameter map; smoothing and clustering the raw parameter map to create clustered region of interest (ROI) maps; combining the clustered ROI maps with the raw multiphase data to generate clustered ROI mean multiphase data; fitting the clustered ROI mean multiphase data to the function to create parameter prior maps; using the parameter prior maps and the clustered ROI maps as a prior to determine a difference in the parameter offset thereof, and using the difference in the parameter offset for re-fitting magnitude and signal offset for the raw multiphase data to generate preliminary blood flow maps; calibrating the preliminary blood flow maps for absolute blood flow quantification; and generating and outputting final blood flow map images. In an embodiment, the parameter offset is a phase.

In an embodiment, the method can comprise: positioning an imaging scanner in relation to a subject; setting a labeling plane within the subject in which the scanner labels blood; labeling blood in an area of the subject in the labeling plane using a plurality of phase increments and an imaging scanner; acquiring a data set from the labeled blood in the subject using the imaging scanner; reconstructing raw multiphase data from the acquired data set; fitting the raw multiphase data to a function; averaging the fitted data; combining the averaged fitted data with the raw multiphase data; fitting the combined data to a function and correcting for parameter offsets; calibrating the fitted combined data for absolute blood flow quantification; and generating and outputting final blood flow maps, wherein the final blood flow maps comprise quantitative blood flow information. In an embodiment, the parameter offsets are phase offsets.

In an embodiment, the system can comprise: a magnetic resonance (MR) imaging scanner; at least one computing device having a processor and a memory; and at least one application executable in the at least one computing device stored in the memory that, upon positioning the imaging scanner in relation to a subject and setting a labeling plane within the subject in which the scanner labels blood, when executed by the processor, the application causes the computing device to at least: label blood in an area of the subject in the labeling plane using a plurality of phase increments and the imaging scanner; acquire a multiphase data set from the labeled blood in the subject using the imaging scanner; reconstruct raw multiphase data from the acquired data set; fit the raw multiphase data to a function; average the fitted data; combine the averaged fitted data with the raw multiphase data; fit the combined data to a function and correct for phase offsets; calibrate the corrected fitted combined data for absolute blood flow quantification; and generate and output final blood flow maps, wherein the final blood flow maps comprise quantitative blood flow information.

In an embodiment, the system can comprise: a magnetic resonance (MR) imaging scanner; at least one computing device having a processor and a memory; and at least one application executable in the at least one computing device stored in the memory that, upon positioning the imaging scanner in relation to a subject and setting a labeling plane within the subject in which the scanner labels blood, when executed by the processor, the application causes the computing device to at least: label blood of the subject in the labeling plane with the imaging scanner with arterial spin labeling using a plurality of phase increments; acquire a data set from the labeled blood in the subject using the imaging scanner; reconstruct raw multiphase data from the acquired data set; fit a function to the raw multiphase data to generate a raw parameter map; smooth and cluster the raw parameter map to create one or more clustered region of interest (ROI) maps; combine the one or more clustered ROI maps with the raw multiphase data to generate clustered ROI mean multiphase data; fit the clustered ROI mean multiphase data to the function to create parameter prior maps; use the parameter prior maps and the one or more clustered ROI maps as a prior to determine a difference in the parameter offset thereof, and use the difference in the parameter offset for re-fitting magnitude and signal offset for the raw multiphase data to generate preliminary blood flow maps; calibrate the preliminary blood flow maps for absolute blood flow quantification; and generate and output final blood flow map images.

In any one or more aspects of the methods or systems, the imaging scanner can be a magnetic resonance scanner with a field strength of about 1.2 T or stronger. A parameter of the raw parameter map can be phase or flow velocity. The clustering can include a grouping of regions of voxels having a commonality of phase parameters, flow velocity parameters, or both. The labeling plane can be in the neck of the subject, offset with respect to the longitudinal axis of the subject by an offset angle and approximately perpendicular to one or more carotid arteries of the subject. The plurality of phase offsets can be separated by a phase angle of about 0 to about 180. The clustering can be voxel, supervoxel clustering, or k-means clustering. The functions can be a fermi function, a modified fermi function, or another function that describes a signal as a function of phase offset. The method can further include processing the final blood flow maps with post-hoc spatial smoothing or spatial regularization, individually or in combination. The final blood flow maps can be maps of cerebral blood flow.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1A:
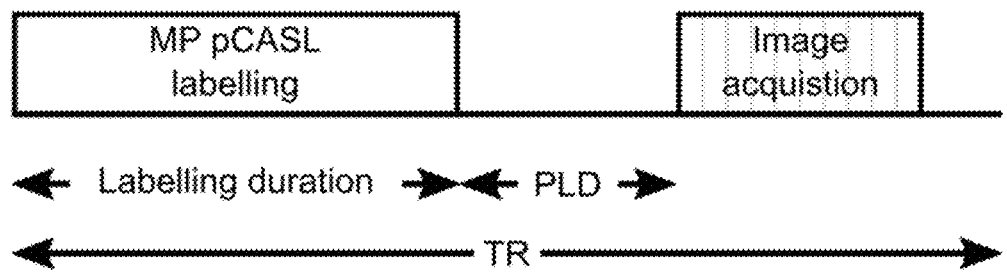
FIG. 1A is a schematic of an embodiment of a multiphase pseudo-continuous arterial spin labeling (PCASL) sequence according to methods as described herein.

Described below are various embodiments of the present systems and methods for multiphase pseudo-continuous arterial spin labeling (multiphase PCASL, MPCASL, or MP PCASL as used herein). Although particular embodiments are described, those embodiments are mere exemplary implementations of the system and method. One skilled in the art will recognize other embodiments are possible. All such embodiments are intended to fall within the scope of this disclosure. Moreover, all references cited herein are intended to be and are hereby incorporated by reference into this disclosure as if fully set forth herein. While the disclosure will now be described in reference to the above drawings, there is no intent to limit it to the embodiment or embodiments disclosed herein. On the contrary, the intent is to cover all alternatives, modifications and equivalents included within the spirit and scope of the disclosure.

Discussion

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for.

It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.
Description In conventional arterial spin labeling (ASL), the inversion of blood water, for example in the neck, can be followed by a long post-labeling delay (PLD) to allow the blood to reach the tissue before separate image acquisition. When such images are subtracted from "control" images, in which the blood water was not inverted, images of perfusion can be obtained. This methodology can be crude, and can generate blood flow maps that are not an accurate depiction of blood flow in the region of interest.

It is now widely accepted that pseudo-continuous labelling is a preferred scheme for ASL perfusion imaging due to increased signal-to-noise-ratio (SNR) over pulsed variants. A short-coming of PCASL, however, is sensitivity to artefacts such as phase mismatch due to the presence of off-resonance fields, and blood flow velocity in the labelling plane; this can lead to inefficient labelling, resulting, in the worst case, in the loss of perfusion information in a whole perfusion territory fed, or at least variations in labelling efficiency for blood destined for different regions of the brain, not routinely accounted for in quantification methods.

Phase mismatch can be reduced by effective shimming in the labelling region, something that is not routine as shimming is more commonly applied only to the imaging region. Since phase mismatch is directly related to field homogeneity it is particularly acute at higher field strength and thus of particular relevance to the increasing use of PCASL in certain scenarios, such as at 7 T in humans, as well as the use at even higher fields pre-clinically in small animal studies.

Methods have been previously proposed to correct for the effect using a BO field map, for example, to measure the labelling efficiency in individuals. More recently a method to measure inversion efficiency in individual arteries using a separate short ASL scan has been presented, but only demonstrated for the internal carotid arteries. These methods permit post-hoc correction for phase mismatch along, where inversion efficiency is measured directly, with outer sources of variation in inversion efficiency. However, these methods are not ideal as they either provide a global correction for the whole brain, or artery specific information that cannot simply be applied to the data since the perfusion territories may not be known.

An alternative solution can be to acquire data at a range of phase offsets and then reconstruct the perfusion image taking into account the variation in labelling efficiency with phase offset, as described in a 2010 publication by Jung et. al (Y. Jung, E. C. Wong, and T. T. Liu, "Multiphase pseudo-continuous arterial spin labeling (MP-PCASL) for robust quantification of cerebral blood flow," *Magn Reson Med*, vol. 64, no. 3, pp. 799-810, September 2010) [13]. This strategy offers an overall lower temporal efficiency than ideal PCASL labelling because data is acquired in a range of suboptimal control/label conditions. However, this scheme can be applied voxel-wise to correct for the effects of phase mismatch as apply to the labelled blood-water that has supplied each voxel. Additionally, in principle, this method can allow for the estimation of flow velocity in the labelled arteries through knowledge of the relationship between signal at different phase offsets and flow velocity, although SNR limitations prevented this being sufficiently robust at 3T, as shown in other studies.

The accuracy of perfusion measurements arising from model fitting, such as that described by Jung above, is dependent upon the SNR of the data. However, this is not purely a random effect as might be supposed, but at the SNR reduces a bias in the parameters of the model fit are observed. This has not previously been recognised for MP PCASL, but is consistent with studies that have been performed on the fitting of a sinusoidal profile to data with additive nose and a limited number of samples.

In a recent preclinical study at 9.4 T (Example 1 below), a multi-phase PCASL strategy was adopted and sought to validate ASL perfusion measurements in rodents against gold-standard autoradiography. As part of that study, limitations were discovered in the current approach to multi-phase PCASL perfusion quantification as described by Jung that have not previously been apparent. These limitations would prevent the accurate quantification of blood flow and inaccurate blood flow maps according to the previous methodologies. Examination of the limitations as described herein led to a new quantification scheme that incorporated a robust detection of phase offset information from perfusion images exploiting recent machine learning representations of data in the form of supervoxels and clustering. Using this scheme the PCASL perfusion measurements were in line of those from autoradiography, which is widely considered the gold standard for quantitative perfusion measurements.

Described herein are technical details of the scheme adopted in the work of Example 1, illustrating the technical issues and a robust solution. Although examples as described herein relate to phase offsets, methods as described herein can be applied to other parameters using other functions, such as flow velocity estimation in feeding arteries and for example employing a flow velocity parameter.

In certain aspects, a pseudo-continuous or continuous imaging approach is provided herein where the labeled blood can be tracked throughout its path from one or more vessels all the way into tissue. In an aspect, labeled blood can be tracked throughout its path from the neck all the way into the brain tissue.

Systems and methods as described herein are an improvement upon traditional ASL or pseudo-continuous ASL (PCASL) methods relying on traditional label-control subtraction to determine blood flow. In one or more aspects, systems and methods as described herein present improvements in existing methodologies by accounting for phase mismatch due to the presence of off-resonance fields, and blood flow velocity in the labelling plane; accounting for phase mismatch leads to more efficient labelling, resulting, in improved and more accurate perfusion information in a whole perfusion territory fed, and therefore improved quantification methods. Systems and methods as described herein additionally provide improvements by providing better perfusion images from imaging scanners, and improve operability of device hardware (and associated computing devices) in at least those regards.

In certain aspects, systems and methods as described herein are suitable for generating maps of perfusion. In certain aspects, maps of perfusion (or perfusion maps) that when in the brain relate to cerebral blood flow (CBF). In certain aspects, maps of cerebral blood flow generated and outputted by systems and methods as described herein comprise quantified cerebral blow flow information.

Systems and methods as described herein can utilize multi-phase PCASL, which involves the acquisition of images over a range of phase offsets for pseudo-continuous labelling applied to a plane through a subject or a portion of a subject. The plane can contain one or more arteries in the subject. In certain aspects, systems and methods as described herein can utilize multi-phase PCASL, which involves the acquisition of images over a range of phase offsets for pseudo-continuous labelling applied to a plane through the neck intersecting the major arteries feeding the brain. The resulting images can contain a common static tissue contribution plus a modulated contribution from partially labelled blood.

Labeling of the blood can be accomplished with a plurality of phase offsets. In certain aspects, two or more phase offsets are used. The range of phase offsets can be about 0 to about 360 degrees. Phase offsets can be separated from each other by a phase angle of within about 0 to about 180 degrees.

Labeling of the blood can be accomplished using an imaging scanner. In certain embodiments, the imaging scanner is a magnetic resonance imaging (MRI) scanner with a field strength of about 1.2 T or greater, including for example 3 T, 7 T and 9.4 T.

Labeling of the blood using the imaging scanner can be accomplished within a labeling plane. The labeling plane can be placed at an offset relative to the longitudinal axis of a subject. In an embodiment, the labeling plane can be placed at an offset of about 45° relative to the longitudinal axis of a subject. In other aspects, the labeling plane can be placed at an offset of about 0 to about 180 degrees relative to the longitudinal axis of a subject or anywhere there between.

Systems and methods as described herein can be utilized on one or more subjects in clinical or pre-clinical settings. As used herein, a subject can refer to any living organism having a vascular system in which fluids circulate. In embodiments, a subject of systems and methods as described herein is a rodent (such as a species of mouse or rat) or a non-human primate. In embodiments, a subject is a human.

In certain aspects, the labeling plane can interset one or more arteries in the subject. The one or more arteries can be in the neck of the subject. In certain aspects, the labeling plane is positioned with respect to a subject so that it is about perpendicular to one or more arteries in the subject. In certain aspects, the labeling plane is positioned with respect to a subject so that it is about perpendicular to one or more arteries in the neck of the subject. In certain aspects, the labeling plane is positioned with respect to a subject so that it is about perpendicular to one or more carotid arteries in the neck.

In systems and methods as described herein, raw multiphase ASL data, such as multiphase PCASL data, acquired from the imaging scanner and the subject is fit to a function or model. In certain embodiments, this function can be a Fermi function, a modified Fermi function, a sinusoidal function, or other model-fitting function to model the variation of inversion achieved of the blood-water by the labelling pulse train.

In certain embodiments, this can be approximated by a modified Fermi function, described below. In an aspect, by voxelwise fitting of this function (plus an offset to model the static tissue) to the phase offset data, the amplitude can be extracted, providing a measure of optimal label control difference and hence perfusion. In other aspects, other parameters, such as flow velocity, can be approximated by model fitting the raw multiphase data to other functions.

The accuracy of perfusion measurements arising from model fitting can be dependent upon the SNR of the data. However, this is not purely a random effect as might be supposed, but as the SNR reduces a bias in the parameters of the model fit are observed.

In reality the Fermi function description may only provide approximation to the real variation with phase offset. This results in a numerical description of the profile that can be fit to the data and allows the flow velocities of the blood in the arteries to be taken into account. The subtle effect of flow velocity means that relatively high SNR may be needed for estimation of this parameter.

After fitting the raw multiphase data to a model, or function, the fitted data can be smoothed, averaged, or otherwise clustered in part to increase SNR. Voxel, supervoxel or k-means clustering can be used to cluster the fitted data, although other methodologies may be employed. Following clustering, it is anticipated that regions of the brain which are fed by the same arteries may have the same phase offset. For example, regions (ROI's) of voxels or supervoxels can be grouped or clustered. The voxels or supervoxels for clustering together can be selected based on a selected commonality of phase parameters. Thus, in an aspect it can be phase or phase offset that can be sought for identification on a per ROI (and in principle on a per artery) basis. For example, each feeding artery to the brain can be anticipated to have a phase offset. The feeding arteries for grouping together can be selected based on having similar or common offsets.

After clustering the data, the clustered data can be combined with the raw data, and model fitting be implemented again to estimate the model parameters within the newly defined region(s). A subset of these parameters, such as the phase parameter (for example), can then be used as prior information for further analysis. Using the parameter prior maps and the clustered maps as a prior to determine a difference in the phase offset thereof, and using the difference in the phase offset for re-fitting magnitude and offset for correcting the raw multiphase data, one or more preliminary blood flow maps can be generated based on the corrected raw multiphase data. In an embodiment, an average phase offset of the clustered data can be determined and the difference between the determined average offset of the clustered data of the raw multiphase data can be used in the re-fitting of the multi-phase data to correct a phase mismatch in the raw data to generate blood flow maps of the subject.

The preliminary blood flow maps can then be calibrated for absolute blood flow quantification and final blood flow maps generated and outputted by the systems and methods. Final blood flow maps can comprise information of quantification of blood flow.

Systems and methods as described herein can additionally utilize post-processing of the blood flow maps, such as with post-hoc spatial smoothing or spatial regularization, individually or in combination.

In imaging schemes according to the present disclosure, the ASL signal can be rapidly attenuated, leading to poor SNR at later time points. This may be particularly problematic for spoiled gradient echo (SPGR) techniques, because part of the ASL signal may be destroyed each time it is sampled. This effect can be much less exaggerated for methods based on highly efficient balanced steady-state free precession (bSSFP), meaning that high SNR can be sustained over a longer period of acquisition time. However, bSSFP is more sensitive to magnetic field inhomogeneity introduced by the presence of the patient in the scanner. In addition, high signal strength can be maintained at later time points by varying the flip angle of the radio-frequency (RF) pulses used to generate the MRI signal, at the cost of lower signal strength at earlier time points. A similar trade-off may be involved for the RF pulse repetition time, TR: a short TR means data are acquired more rapidly, at the cost of greater signal attenuation. Simulations can be used to optimize the variable flip angle schedule and other image acquisition parameters to reduce signal attenuation, ensure high SNR, and robustness to field inhomogeneity. Constant flip angles or variable flip angles can be used in the herein described system and method.

The present approach is not limited to use of pseudo-continuous ASL (PCASL) labeling. In various aspects, other ASL labeling techniques can be used. These can include the use of a time-encoded (also known as Hadamard encoded) ASL, a vessel-selective ASL preparation, or labeling in which the blood in each feeding artery can be uniquely encoded allowing their contributions to the downstream signal to be extracted in post-processing. This can allow imaging of collateral blood flow and arterial supply to lesions, but can also lead to increases in scan time because the number of encoded images required is proportional to the number of arteries of interest.

Therefore, in various aspects, provided herein are systems and methods of pseudo-continuous ASL utilizing multiphase labeling. Systems and methods as described herein are suitable for a variety of subjects in pre-clinical and/or clinical settings, and provide improvements in blood flow measurements, especially the accurate quantification thereof.

In certain embodiments, MP PCASL can involve the acquisition of images over a range of phase offsets for pseudo-continuous labelling applied to a plane through the neck intersecting the major arteries feeding the brain. The resulting images contain a common static tissue contribution plus a modulated contribution from partially labelled blood, which can be approximated by a modified Fermi function (Eq. 1 below):

$$f(x) = -2\left(\frac{1}{1+e^{\frac{|x|-\alpha}{\beta}}}\right)+1 \qquad \text{(Eq. 1)}$$

In certain aspects, by voxel-wise fitting of this function (plus an offset to model the static tissue) to the phase offset data the amplitude can be extracted, providing a measure of optimal label control difference and hence perfusion.

In certain aspects, the Fermi function description is only an approximation to the real variation with phase offset. A more accurate model can be derived by modelling parameters and interactions thereof, such as the flow and interaction with the PCASL labelling pulses. This can result in a numerical description of the profile that can be fit to the data and can allow the flow velocities of the blood in the arteries to be further taken into account. The subtle effect of flow velocity means that relatively high SNR is needed for estimation of this parameter, hence it has thus far not been successful for voxel-wise estimation from MP PCASL perfusion imaging at 3 T in humans in previous work. Although this has been used in a technique for vessel-encoded PCASL (VEPCASL) analysis where parameter estimation was effectively performed across a whole perfusion territory, thus increasing the SNR by averaging of multiple voxels. The similarity of the Fermi and sinusoidal functions has previously been established and used in early analysis of the related vessel-encoded PCASL methods.

In certain aspects, the fitting of the modified Fermi function to MP PCASL data can involve the estimation of three parameters (Eq. 2 below):

$$\Delta M(\theta) = Af(\theta-\phi)+B \qquad \text{(Eq. 2)}$$

where theta is the phase offset at which measurement(s) occurred; A is the amplitude of the modified Fermi function contribution and provides a measure of the perfusion in an ROI or voxel as would be measured with ideal label and control subtraction, B is the signal offset due to static tissue contribution and phi is the phase associated with the artery in which labelling was performed for the ROI or voxel.

In certain aspects, unbiased estimation of MP PCASL model parameters can only be achieved with sufficient SNR and this is unlikely to be realised voxel-wise from ASL data. To get an unbiased estimate irrespective of SNR it is only necessary to know one of the three parameters. Hence, in an aspect, phase offset can be estimated robustly from a larger ROI, in which multiple voxels can be averaged first, and then proceed to voxelwise perfusion estimation with this parameter fixed. In other aspects, one of the other parameters might be estimated. The ROIs required can correspond to the perfusion territories supplied by each of the arteries in the labelling plane. Whilst there is a fair degree of consistency in these in both humans and rodents, the boundaries of these territories cannot be guaranteed, especially in pathology. Whilst they could be assessed using VEPCASL, this would largely defeat the object of using MP PCASL, essentially replacing it with a longer duration scan.

In certain aspects, whilst there is an inherent bias in the estimation of phase offset from voxelwise MP PCASL data, differences in phase offset are preserved. Thus, if two perfusion territories were fed with arteries with different phase mismatch this can be seen in the resulting map, even if the absolute values were incorrect. This result can be exploited to define the ROIs based on a first (biased) model-based analysis of the data. To robustly define ROIs from the resulting phase offset map, a supervoxel algorithm can be applied to group regions of common spatial appearance (parameters of the grid) and then cluster the voxels using k-means with four classes (to represent the 4 feeding arteries labelled) as this is what happens in a brain mask. With the ROIs defined the multi-phase data in each ROI is averaged and model fitting performed. The resulting phase offset values can then be used as fixed estimates in a final voxelwise model fitting of the data.

In certain aspects, model-fitting can be performed using the Fermi-function of equation as shown herein with the alpha and beta values from using a variational Bayesian non-linear model inference method implemented in the fabber program that is distributed as part of the BASIL toolbox for ASL perfusion quantification in the FMRIB Software Library. The alpha and beta values can be determined as in the Jung et al paper [13]. They can also be determined from published literature values, based on preliminary analysis and/or by study-specific determination of the values. Perfusion quantification can be performed using BASIL, according to the standard model of Buxton et al. and a reference region calculation of the equilibrium magnetisation of arterial blood within a species-specific brain region. The full method, including model-fitting, supervoxel analysis and clustering can be implemented in Quantiphyse.

Furthermore, in other embodiments, the methodologies outlined above can be extended to simultaneously estimate flow velocity in feeding arteries by replacing the Fermi function with a model of the expected flow profile generated by simulation of the degree of labeling with phase offsets achieved by the phase labeling pulses [15]. Profiles can be generated for flow velocities of values and phase offsets of values. This matrix of solutions can be loaded into the fabber program and linear interpolation used to evaluate the model at values between those simulated. All parameters can be fit in the first stage of the data analysis and then after ROI generation in the ROIs. Values of phase offset and flow velocity for each ROI can then be fixed for the final analysis of the voxels within each ROI to derive the final perfusion images.

System and Apparatus

Figure 13:
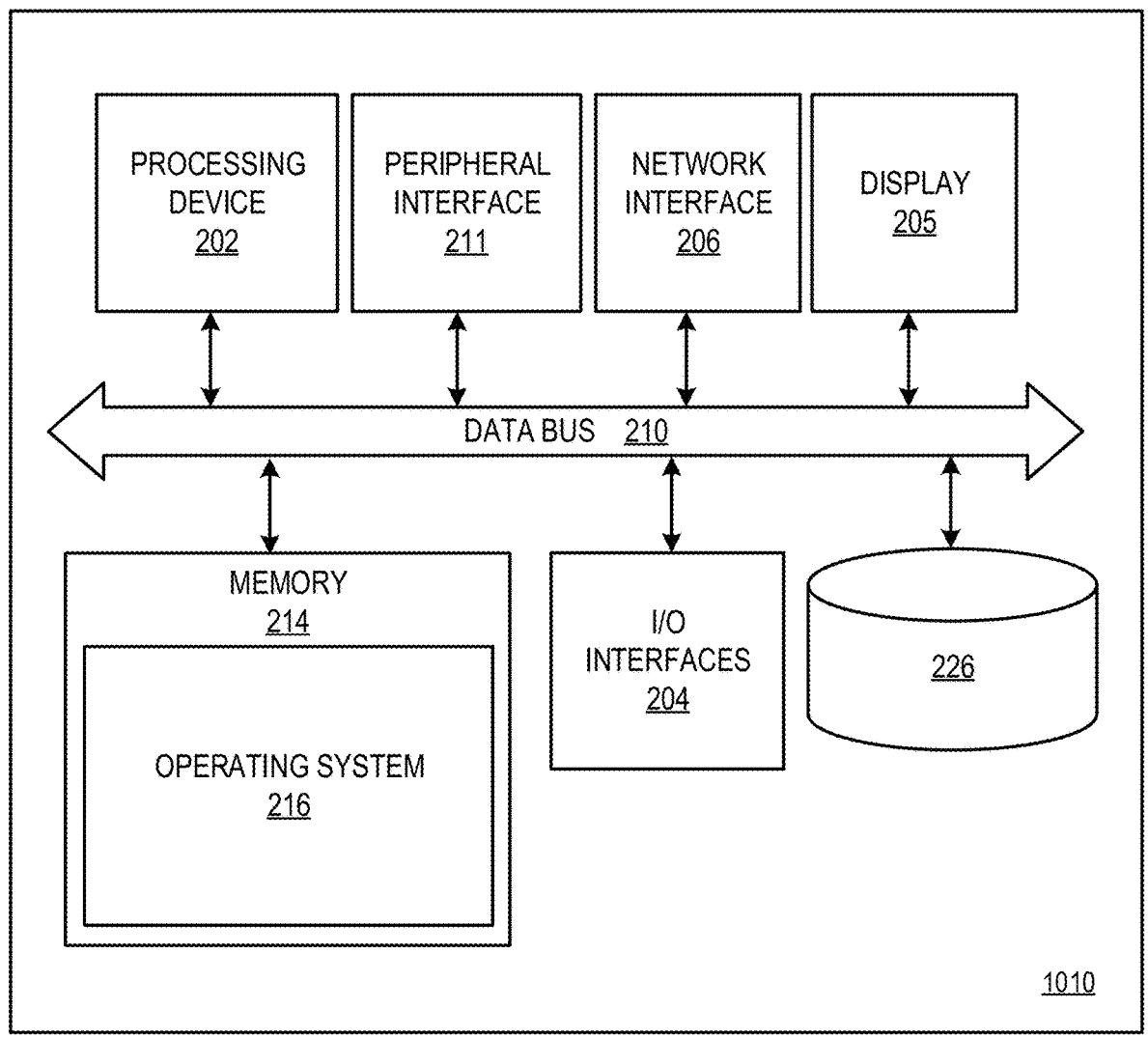
FIG. 13 is an embodiment of a computing device according to systems and methods disclosed herein.

Reference is now made to FIG. 13, which depicts an apparatus 1010 in which the systems and methods for combined angiography and perfusion imaging described herein may be implemented. The apparatus 1010 may be embodied in any one of a wide variety of wired and/or wireless computing devices, multiprocessor computing device, and so forth. As shown in FIG. 13, the apparatus 1010 comprises memory 214, a processing device 202, one or more input/output interfaces 204, a network interface 206, a display 205, a peripheral interface 211, and mass storage 226, wherein each of these devices are connected across a local data bus 210. The apparatus 1010 may be coupled to one or more peripheral measurement devices (not shown) connected to the apparatus 1010 via the peripheral interface 211.

The processing device 202 may include any custom made or commercially available processor, a central processing unit (CPU) or an auxiliary processor among several processors associated with the apparatus 1010, a semiconductor based microprocessor (in the form of a microchip), a macroprocessor, one or more application specific integrated circuits (ASICs), a plurality of suitably configured digital logic gates, and other well-known electrical configurations comprising discrete elements both individually and in various combinations to coordinate the overall operation of the computing system.

The memory 214 can include any one of a combination of volatile memory elements (e.g., random-access memory (RAM, such as DRAM, and SRAM, etc.)) and nonvolatile memory elements (e.g., ROM, hard drive, tape, CDROM, etc.). The memory 214 typically comprises a native operating system 216, one or more native applications, emulation systems, or emulated applications for any of a variety of operating systems and/or emulated hardware platforms, emulated operating systems, etc. For example, the applications may include application specific software which may be configured to perform some or all of the systems and methods herein. In accordance with such embodiments, the application specific software is stored in memory 214 and executed by the processing device 202. One of ordinary skill in the art will appreciate that the memory 214 can, and typically will, comprise other components which have been omitted for purposes of brevity.

The one or more input/output interfaces 204 provide any number of interfaces for the input and output of data. For example, where the apparatus 1010 comprises a personal computer, these components may interface with one or more user input devices 204. The display 205 may comprise a computer monitor, a plasma screen for a PC, a liquid crystal display (LCD) on a hand held device, a touch screen or other display device.

In an embodiment of this disclosure, a non-transitory computer-readable medium stores programs for use by or in connection with an instruction execution system, apparatus, or device. More specific examples of a computer-readable medium may include by way of example and without limitation: a portable computer diskette, a random access memory (RAM), a read-only memory (ROM), an erasable programmable read-only memory (EPROM, EEPROM, or Flash memory), and a portable compact disc read-only memory (CDROM) (optical).

With further reference to FIG. 13, network interface device 206 comprises various components used to transmit and/or receive data over a network environment. For example, the network interface 206 may include a device that can communicate with both inputs and outputs, for instance, a modulator/demodulator (e.g., a modem), wireless (e.g., radio frequency (RF)) transceiver, a telephonic interface, a bridge, a router, network card, etc.). The apparatus 1010 may communicate with one or more computing devices (not shown) via the network interface 206 over the network 118 (not shown). The apparatus 1010 may further comprise mass storage 226. The peripheral 211 interface supports various interfaces including, but not limited to IEEE-1394 High Performance Serial Bus (Firewire), USB, a serial connection, and a parallel connection.

The apparatus 1010 shown in FIG. 13 may be embodied, for example, as a magnetic resonance apparatus, which includes a processing module or logic for performing conditional data processing, and may be implemented either off-line or directly in a magnetic resonance apparatus. For such embodiments, the apparatus 1010 may be implemented as a multi-channel, multi-coil system with advanced parallel image processing capabilities, and direct implementation makes it possible to generate images, for example, immediate T1 maps, available for viewing immediately after image acquisition, thereby allowing re-acquisition on-the-spot if necessary. Examples of apparatus in which the present systems and methods may be implemented are described in U.S. Pat. Nos. 5,993,398 and 6,245,027 and U.S. Publication No. 2011/0181285, which are incorporated by reference as if fully set forth herein.

Figure 14:
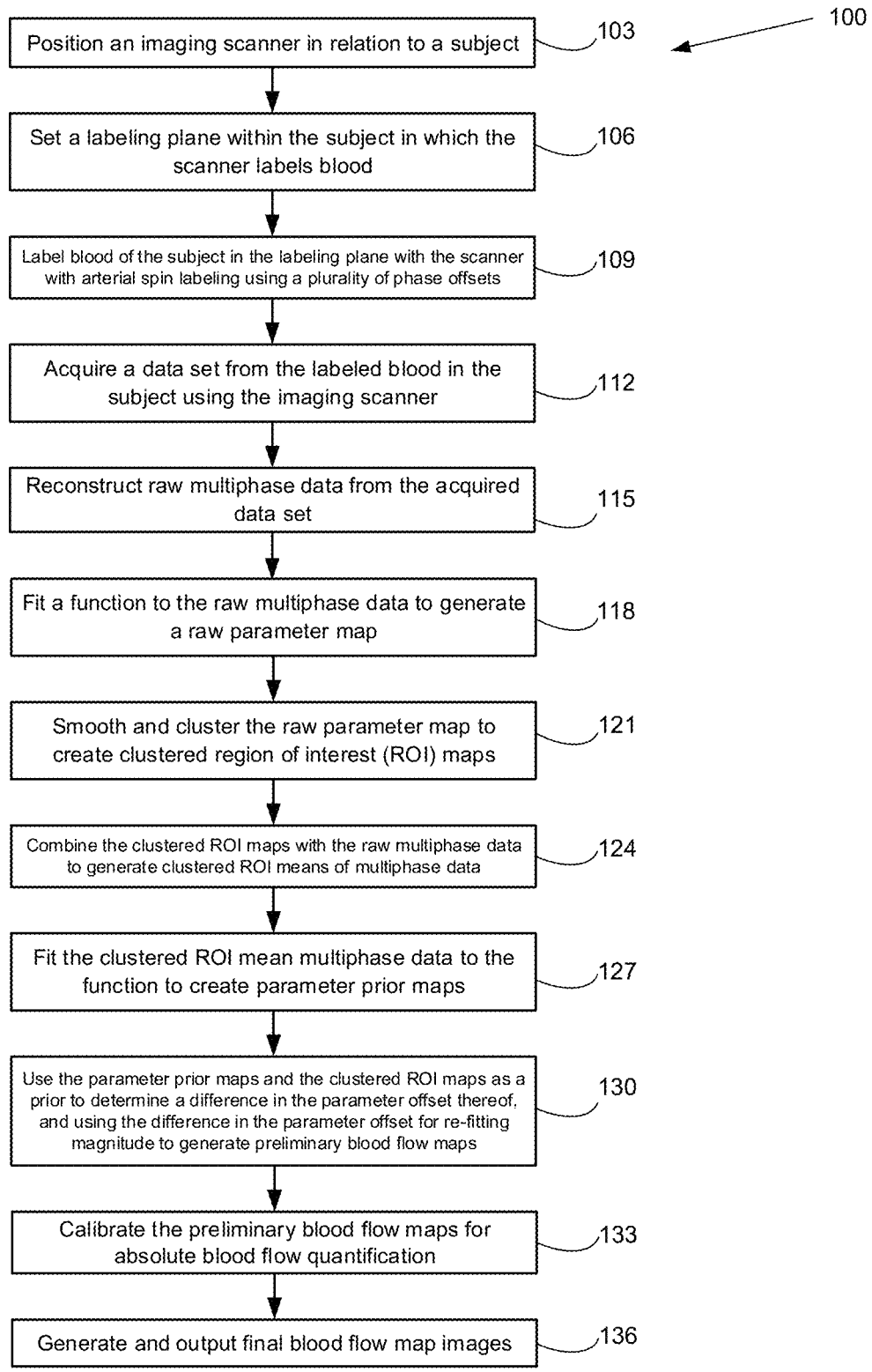
FIG. 14 is a flow chart of an embodiment of the present methods.
Figure 15:
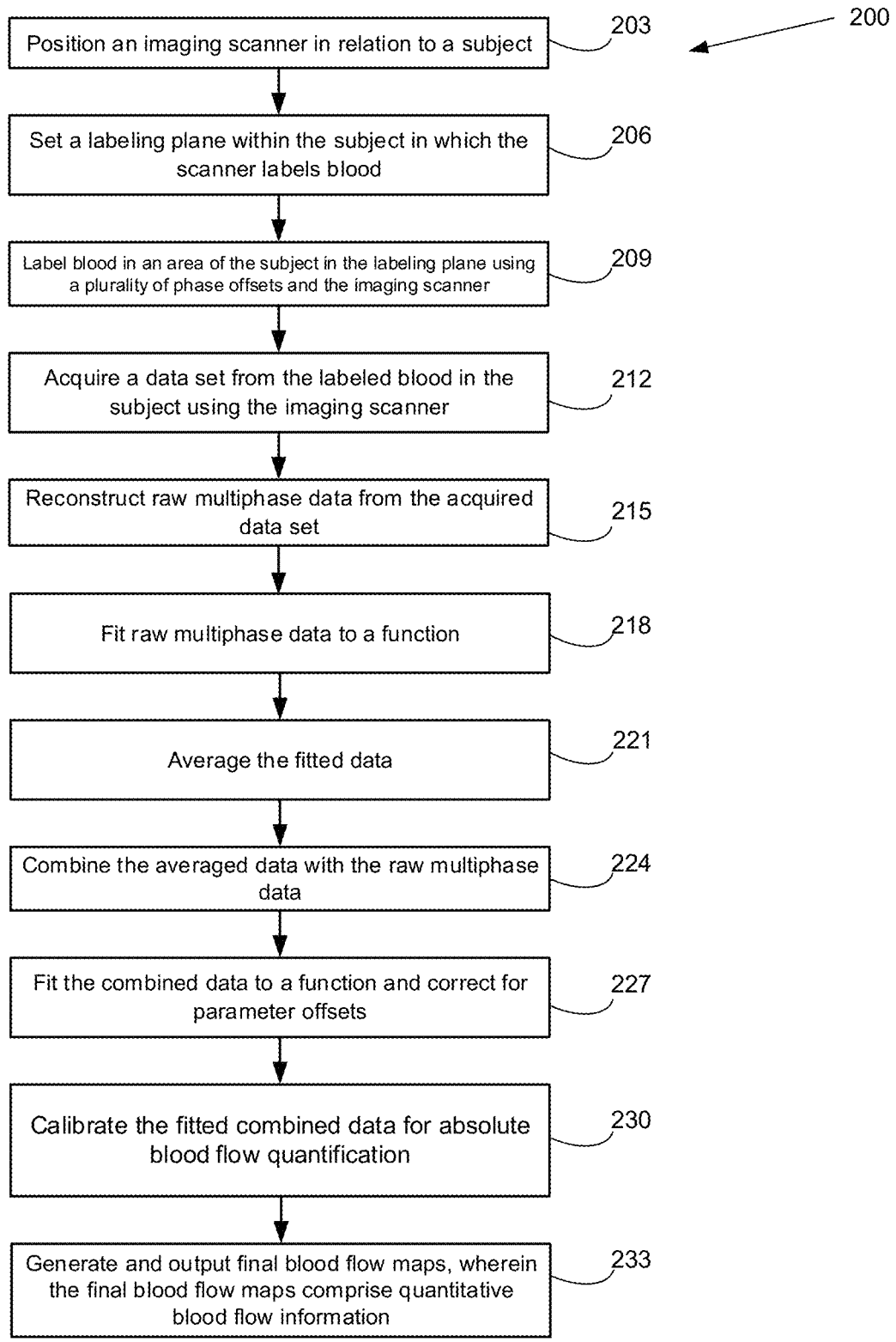
FIG. 15 is a flow chart of an embodiment of the present methods.

The flow charts of FIG. 14 and FIG. 15 show examples of functionality that may be implemented in the apparatus 1010 of FIG. 13. If embodied in software, each block shown in FIG. 14 and FIG. 15 may represent a module, segment, or portion of code that comprises program instructions to implement the specified logical function(s). The program instructions may be embodied in the form of source code that comprises machine code that comprises numerical instructions recognizable by a suitable execution system such as the processing device 202 (FIG. 13) in a computer system or other system. The machine code may be converted from the source code, etc. If embodied in hardware, each block may represent a circuit or a number of interconnected circuits to implement the specified logical function(s).

Although the flowcharts of FIG. 14 and FIG. 15 shows a specific order of execution, it is understood that the order of execution may differ from that which is depicted. For example, the order of execution of two or more blocks may be scrambled relative to the order shown. Also, two or more blocks shown in succession in FIG. 14 and FIG. 15 may be executed concurrently or with partial concurrence. Further, in some embodiments, one or more of the blocks shown in FIG. 14 and FIG. 15 may be skipped or omitted. In addition, any number of counters, state variables, warning semaphores, or messages might be added to the logical flow described herein, for purposes of enhanced utility, accounting, performance measurement, or providing troubleshooting aids, etc. It is understood that all such variations are within the scope of the present disclosure.

Also, any logic or application described herein that comprises software or code can be embodied in any non-transitory computer-readable medium for use by or in connection with an instruction execution system such as, for example, a processing device 202 in a computer system or other system. In this sense, each may comprise, for example, statements including instructions and declarations that can be fetched from the computer-readable medium and executed by the instruction execution system.

In an embodiment, methods as described herein can be comprised of the following steps: raw multiphase data can be fit to a fermi or modified Fermi function with low precision priors to generate a raw phase map; data from the raw phase map can be smoothed and averaged using supervoxel clustering to generate supervoxel region of interest (ROI) maps, in a 3D rendering and/or 2D slice; the supervoxel ROI's can then be combined with the raw multiphase data to yield supervoxel-ROI means of multiphase data (with a high signal-to-noise ratio or SNR); the supervoxel ROI mean multiphase data can then be fit to the Fermi function to generate a phase prior map for final fitting; using the supervoxel ROI phase maps as a high precision prior, the magnitude and offset can be re-fit for the raw multiphase data; images (or maps) can then be calibrated for absolute blood flow quantification (which can be cerebral blood flow, or blood flow in other regions of a subject).

In an embodiment, a method 100 of multiphase PCASL is presented in FIG. 14. In the method 100, an imaging scanner can be positioned in relation to a subject (103). This can be accomplished in several different ways, and is not limited to inside a computing environment as a healthcare professional can manually position the scanner in relation to a subject. After positioning is complete, a labeling plane within the subject in which the scanner labels blood is set (106). Then blood of the subject in one or more vessels is labeled in the labeling plane with the scanner using arterial spin labeling (which can be PCASL) using a plurality of phase offsets (109). A data set can then be acquired from the labeled blood in the subject using the imaging scanner (112). Following data acquisition, data can be transformed from an acquired data set and reconstructed as one or more raw multiphase maps (115). The raw multiphase data can then be fit to a function to generate a raw parameter map (118). The raw parameter map can then be smoothed and clustered to create one or more clustered region of interest (ROI) maps (121). The clustered ROI maps can be combined with the raw multiphase data to generate clustered ROI means of multiphase data (124). The clustered ROI mean multiphase data can then be fit to the function to create parameter prior maps (127). Using the parameter prior maps and the clustered ROI maps as a prior, the difference in a parameter offset thereof can be determined and preliminary blood flow maps can be generated using the difference in the parameter offset for re-fitting the magnitude (130). The preliminary blood flow maps can then be calibrated for absolute blood flow quantification (133), and final blood flow maps (ie images) can be generated and output by the imaging scanner (136).

In another embodiment, a method 200 of multiphase PCASL is presented in FIG. 15. In the method 200, an imaging scanner can be positioned in relation to a subject (203). This can be accomplished in several different ways, and is not limited to inside a computing environment as a healthcare professional can manually position the scanner in relation to a subject. After positioning is complete, a labeling plane within the subject in which the scanner labels blood is set (206). Then blood of the subject in one or more vessels is labeled in the labeling plane with the scanner using arterial spin labeling (which can be PCASL) using a plurality of phase offsets (209). A data set can then be acquired from the labeled blood in the subject using the imaging scanner (212). Raw multiphase data can be reconstructed (ie transformed) from the acquired data set (215), and the raw multiphase data can be fit to a function (218) and averaged (221). The averaged data can then be combined with the raw multiphase data (224), and the combined data can be fit the the function and corrected for one or more parameter offsets (227). The fitted combined data can then calibrated for absolute blood flow quantification (230). Following calibration, final blood flow maps (ie images) can be generated and output from the imaging scanner, wherein the final blood flow maps contain quantitative blood flow information (233).

EXAMPLES

Now having described various embodiments of the disclosure, in general, the examples below describe some additional embodiments. While embodiments of the present disclosure are described in connection with the examples and the corresponding text and figures, there is no intent to limit embodiments of the disclosure to these descriptions. On the contrary, the intent is to cover all alternatives, modifications, and equivalents included within the spirit and scope of embodiments of the present disclosure Example 1

Cerebral blood flow (CBF) is an important parameter requiring reliable and accurate quantitation in many disease states and functional studies. In humans, reliable and accurate CBF measurements can be obtained using a magnetic resonance imaging (MRI) technique called arterial spin labelling (ASL). However, although rat models are frequently used for preclinical studies of both human disease and brain function, rat CBF measurements show poor consistency between studies, possibly a partial consequence of their smaller size, differing head geometry and the higher magnetic field strengths typically used in preclinical MRI studies, but also a consequence of differing analysis methodologies.

To address these issues, a multiphase pseudo-continuous ASL (MP PCASL) technique as described herein is implemented, optimised and validated, which overcomes many of the current limitations of rat CBF measurements primarily by using eight phases instead of the two used in conventional label-control ASL MRI. Parameters were optimised to obtain reliable, high quality and accurate CBF maps in three different strains of rat (Wistar, Sprague Dawley and Berlin-Druckrey IX), and CBF values were validated against gold-standard autoradiography measurements. A label positioning was found to be suitable directly behind the medulla oblongata at a 45° angle to allow labelling perpendicular to vessels, whilst the post-label delay was optimised to 0.55 s on the basis that arrival times were <0.55 s in 99% of voxels in the imaging slices. Multiphase PCASL whole brain CBF measures were 116±10, 110±9 and 109±8 mL/100 g/min in Wistar, SD and BDIX rats respectively. Autoradiography CBF measures were: 108±12, 116±14 and 122±16 mL/100 g/min in Wistar, SD and BDIX rats respectively. There was <7% discordance between autoradiography and multiphase PCASL measurements of CBF in all strains.

1. INTRODUCTION

Arterial spin labelling (ASL) is a non-invasive magnetic resonance imaging (MRI) technique that enables measurement of cerebral blood flow (CBF) using blood-water that is magnetically labelled when flowing through the neck, as an endogenous tracer [1-3]. ASL is increasingly gaining popularity in the clinic for its functional MRI (fMRI) capabilities as well as for perfusion analysis in the brain in diseases such as stroke [4], [5] and cancer [6], [7]. In the decades following its inception, ASL has been widely used in both patients and pre-clinical models of disease, leading to many variations of the technique that can be classified primarily into two types: continuous ASL (CASL) and pulsed ASL (PASL). Despite its apparent simplicity, the many variations of ASL have complicated its implementation in routine clinical practice. To this end, the ASL 'white paper' was published in 2015 and gave recommended clinical guidelines for the purpose of standardising ASL across multiple scanners and centres [8]. The white paper considered many aspects of ASL including hardware requirements, pulse sequence parameters, readout approaches and post-processing methods. Its final recommendations include using a pseudo-continuous ASL (PCASL) labelling approach combined with a single post-label delay (PLD), varying slightly depending on the subject's age and health status.

Simple transposition of the recommended clinical methods to pre-clinical systems, however, is not sufficient to achieve high quality imaging. Interspecies differences mean that a direct transposition of acquisition parameters yields spurious and error-prone data. This poses a significant problem because pre-clinical models of disease are of critical importance in many fields and accurate, non-invasive and quantitative measurement of blood flow is a crucial parameter in many studies. The problems with pre-clinical ASL stem mostly from issues associated with the high field strengths that are used pre-clinically, as well as rodent-specific head and neck geometry. High quality ASL images are dependent upon a uniform magnetic field, not only in the imaging plane, but also in the labelling plane. Off-resonance effects arising from poor magnetic field homogeneity and neck geometry lead to differing labelling efficiency in each vessel in the labelling plane. These efficiencies will be poorer by unknown amounts which results in CBF maps which will contain values which are also erroneous by the same unknown amount—a situation particularly problematic with traditional label-control ASL MRI. This problem is exacerbated in pre-clinical imaging studies for two reasons: (1) the air spaces in rodent heads (throat, esophagus, mouth, and nasal cavities) are very close to the labelling and imaging planes, causing large magnetic susceptibility artefacts and off-resonance effects; and (2) the higher field strengths used (typically ⊄7 T) make it more difficult to create a homogenous magnetic field.

These problems have led to a wide range of published CBF measurements in rodents, often obtained using different variations of ASL MRI. These published values vary considerably and often span ranges that are neither physiologically realistic (e.g. >300 mL/100 g/min [9-11]), nor in agreement with gold-standard autoradiography measures of perfusion [12]. Thus, there is a need to improve the application of ASL MRI in rodents and to achieve a similar standardization to that now implemented clinically.

Multiphase PCASL (MP PCASL), is a variant of ASL where instead of acquiring the traditional label and control images, images are acquired following labelling with radiofrequency (RF) pulses at multiple phase increments [13]. These increments span 360 degrees allowing fitting of the data to an expected function, rather than simply subtracting label from control. These extra phase increments can make the acquisition of MP PCASL more time consuming than a simple label-control experiment. However, in a rodent, where the exact magnetic environment in the labelling plane is unknown and likely to be inhomogeneous, the MP PCASL acquisition offers an ability to correct post hoc for the off-resonance effects in the neck and return true values for CBF. Thus, MP PCASL can offers a way to trade increased scan time for a markedly increased confidence in CBF values.

An aim of the present example, therefore, is to implement, optimise and validate an embodiment of an MP variant of PCASL in rats, in order to improve the accuracy and reliability of rodent CBF measurements. Experiments of the present example were performed in three different strains of rat (Wistar, Sprague Dawley (SD) and Berlin Druckrey IX (BDIX)) to enable robust assessment of the reliability and applicability of the MP PCASL method. CBF measurements were compared to those obtained by $^{14}$C-iodoantipyrine autoradiography, the pre-clinical gold-standard technique for quantitative CBF determination [12], [14].

2. MATERIALS AND METHODS

2.1 Animals

Female Wistar, Sprague Dawley (SD) and Berlin Druckrey IX (BDIX) rats weighing 180-340 g were used. All animal experiments were approved by the UK Home Office.

2.2 Carotid Blood Flow Measurement

Rats (n=9) were anaesthetised with isoflurane and laid supine on an ultrasound stage. Body temperature was maintained at ca. 37° C. through use of a rectal temperature probe and an electrically-heated blanket under the animal. Hair across the neck was removed by clipping and depilatory cream. An MX550D probe coupled to a Vevo 3100 ultrasound (Visualsonics) was used in B-mode and parallel to the rostro-caudal axis to visualise the arteries in the neck. The angle of the carotid arteries with respect to the probe was measured (FIGS. 8A-8B) and the blood velocity calculated using $f_{doppler}=(2 \cdot f_0 \cdot v_{blood} \cdot \cos\theta)/c$, where $f_{doppler}$ is the Doppler frequency, $f_0$ is the transmitted ultrasound frequency, $v_{blood}$ is the blood velocity, c is the speed of sound in tissue (1540 m/s) and $\theta$ is the angle between the probe and the blood vessel. Each animal was observed for 30 seconds at 10-12 respiration rates between 39 and 65 breaths per minute. Acquired videos were used to determine the time-averaged mean and peak blood velocities at each respiration rate.

2.3 Simulations of Arterial Spin Labeling

Numerical simulations using the Bloch equations were conducted using pre-validated code [15] in Matlab (Mathworks, Natick, Mass.) to determine theoretical blood inversion during the ASL pulse sequence (i.e. M(z), expressible as labelling efficiency—the percentage of maximum inversion possible). A PCASL sequence was simulated with a pulse train of 600 μs Hanning-shaped pulses, each separated by 600 μs. Simulated $T_1$ and $T_2$ of blood was 2.1 s and 33 ms, respectively, measured from oxygenated rat blood at 37° C. The ratio $G_{max}/G_{av}$ during labelling was fixed at 20. Blood velocity was simulated from 1-100 cm/s, labelling gradient strengths were varied to correspond to a labelling plane thickness from 2-10 mm and labelling pulse flip angle was varied from 2-90°. The relationship between $G_{max}$ and tagging plane thickness ($Thk_{tag}$) is given by $Thk_{tag}=BW_{trans}/(\gamma_0 \cdot G_{max})$ where $BW_{trans}$ is the transmitted RF bandwidth and $\gamma_0$ is the gyromagnetic ratio (42.58 MHz/T).

2.4 Magnetic Resonance Imaging

Rats were anaesthetised with isoflurane and imaged in a 9.4 T MRI spectrometer (Agilent) using a 72 mm volume transmit coil and a 4-channel surface receive array (Rapid Biomedical). Respiration rate was kept between 40 and 60 breaths per minute by adjusting isoflurane concentration.

Figure 1B:
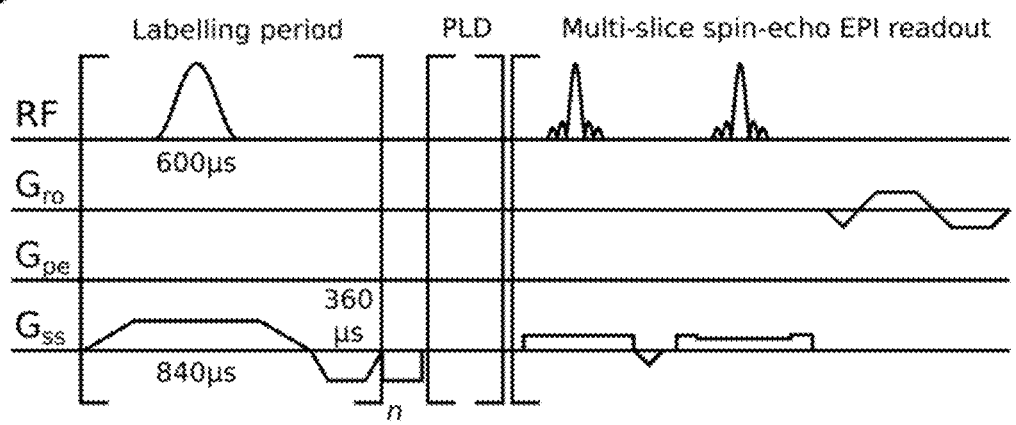
FIG. 1B illustrates a pulse timing diagram of the sequence shown in FIG. 1A.

A multiphase PCASL sequence [13] was implemented by varying the phase increments of pulses in the labelling train from 0° to 315° in 8 steps of 45° degrees. The labelling plane (6.2 mm thick, 4.4 μT $G_{max}$) was placed in the neck of the rat, either perpendicular to, or at 45° to, the animal's rostro-caudal axis. The location of the labelling plane was set through the use of a midline sagittal fast spin echo image (FOV=50×50 mm, matrix=256×256, thickness=2 mm, TR=1 s; $TE_{eff}=40$ ms, $T_{exp}=34$ s). For the MP PCASL, a multislice single-shot spin-echo echo planar imaging (EPI) sequence was used for the imaging readout (FOV=32×32 mm, matrix=64×64, thickness=1 mm, 10 slices, TE=28.7 ms). Slices were acquired in an anterior-posterior (or rostral-caudal) direction. Blood labelling (tagging) was achieved with a pulse train comprising Hanning-shaped pulses of 600 μs duration and 40° flip angle, each separated by 600 μs (50% duty cycle). A schematic of the pulse sequence is shown in FIG. 1A. FIG. 1B is a pulse timing diagram of the sequence shown in FIG. 1A. Proton-density calibration images for absolute CBF quantitation were acquired for all animals, using both the surface receive array and the volume coil, by omitting labelling pulses. For all animals, $T_1$ maps were obtained using an inversion recovery method (inversion time varied in 9 logarithmic steps from 0.013-8 s, TR=10 s) and $T_2$ maps were obtained using a multi-echo approach (echo time varied in 9 logarithmic steps from 30-160 ms, TR=10 s). Readouts were spin echo EPI acquisitions with details the same as for the ASL acquisitions.

Arterial transit time (ATT) was measured by acquiring data with 12 post-label delays (10, 15, 20, 25, 30, 50, 100, 200, 300, 500, 750 and 1000 ms; PLD), each with the same 8 phase angles ($T_{exp}=14$ m 41 s). The spacing of post-label delays was chosen to obtain good fits for typical ATTs observed in pilot data. Multi-PLD images were acquired with only two slices—the first immediately posterior to the olfactory sulcus and the second 10 mm posterior to the first. This was necessary as slices took 50 ms each to acquire each and obtaining 10 slices would lead to an unacceptable minimum delay before acquiring the last slice.

In a subset of animals also used for autoradiography (see Section 2.6), more extensive optimisations were carried out. Label duration was varied as follows: 0.4 s, 0.9 s, 1.4 s (TR=4 s, $T_{exp}=1$ m 29 s); 2.4 s (TR=5 S, $T_{exp}=1$ m 39 s); 3.7 S (TR=6.3 S, $T_{exp}=2$ 4 s); 5.0 s (TR=7.6 s, $T_{exp}=2$ m 30 s), all with a PLD of 550 ms. Label location was varied serially along the neck vasculature in 2 mm increments. To confirm labelling plane location with respect to the brain and brain vasculature, time of flight (TOF) angiography was used to visualise vessels and brain-midline sagittal anatomical MRI was used to show the labelling plane location with respect to the vessels. TOF: $T_1$-weighted 3D gradient echo readout (FOV=40×40×60 mm, matrix=128×128×192, TR=30 ms, FA=30°, axial excitation slab, $T_{exp}=12$ m 17 s). Anatomical MRI: $T_2$-weighted fast spin echo readout (FOV=40×60 mm, matrix=128×192, TR=1 s, $TE_{eff}=10$ ms, single 2 mm slice at brain midline, $T_{exp}=2$ m 8 s).

$T_1$ and 32 times of re-oxygenated post-mortem blood were determined at 37° C. using a heated water jacket sample holder. Oxygenation was confirmed as complete using an i-STAT blood-gas analyser (Abbot, UK).

2.5 Data Fitting and Analysis

ASL data analysis and perfusion quantification was performed using a custom version of BASIL [16] from the FMRIB Software Library (www.fmrib.ox.ac.uk/fsl/basil). The multiphase acquisition data are expected to fit a modified Fermi function of the form:

$$f(x) = \text{Mag}\left(-2\left[\frac{1}{1+e^{(|phase|-\alpha)/\beta}}\right]\right) + \text{Off} \quad \text{(Eq. 3)}$$

where α and β were 70 and 19, respectively; chosen by minimisation of root-mean-square error on data fitting of 12 rats from three strains (data not shown), x is the phase angle in degrees, Mag is the magnitude (amplitude) and Off is the offset from 0 [13]. Fitting was performed using the Variational Bayesian algorithm of {ref Chappell TSP paper} within the FSL tool fabber, which incorporates normally distributed priors on all the parameters. Since 3-parameter models such as this are prone to over-estimation of amplitude in the presence of additive noise [17], a multi-step analysis process was used to minimise bias. Firstly, the raw multiphase data were fitted with unconstrained priors, producing voxel-wise estimates of phase, magnitude and offset. The phase maps were clustered using a supervoxel approach [18] with 4 supervoxels per phase map, a smoothing (a) of 0.8 and a compactness of 0.1. This was used to define ROI from the data that represent individual flow territories as indicated by their phase value arising from the phase offset present in the feeding artery. For each supervoxel region, the original multiphase data was averaged for all voxels across each phase, yielding a new, higher SNR multiphase dataset.

Figure 9:
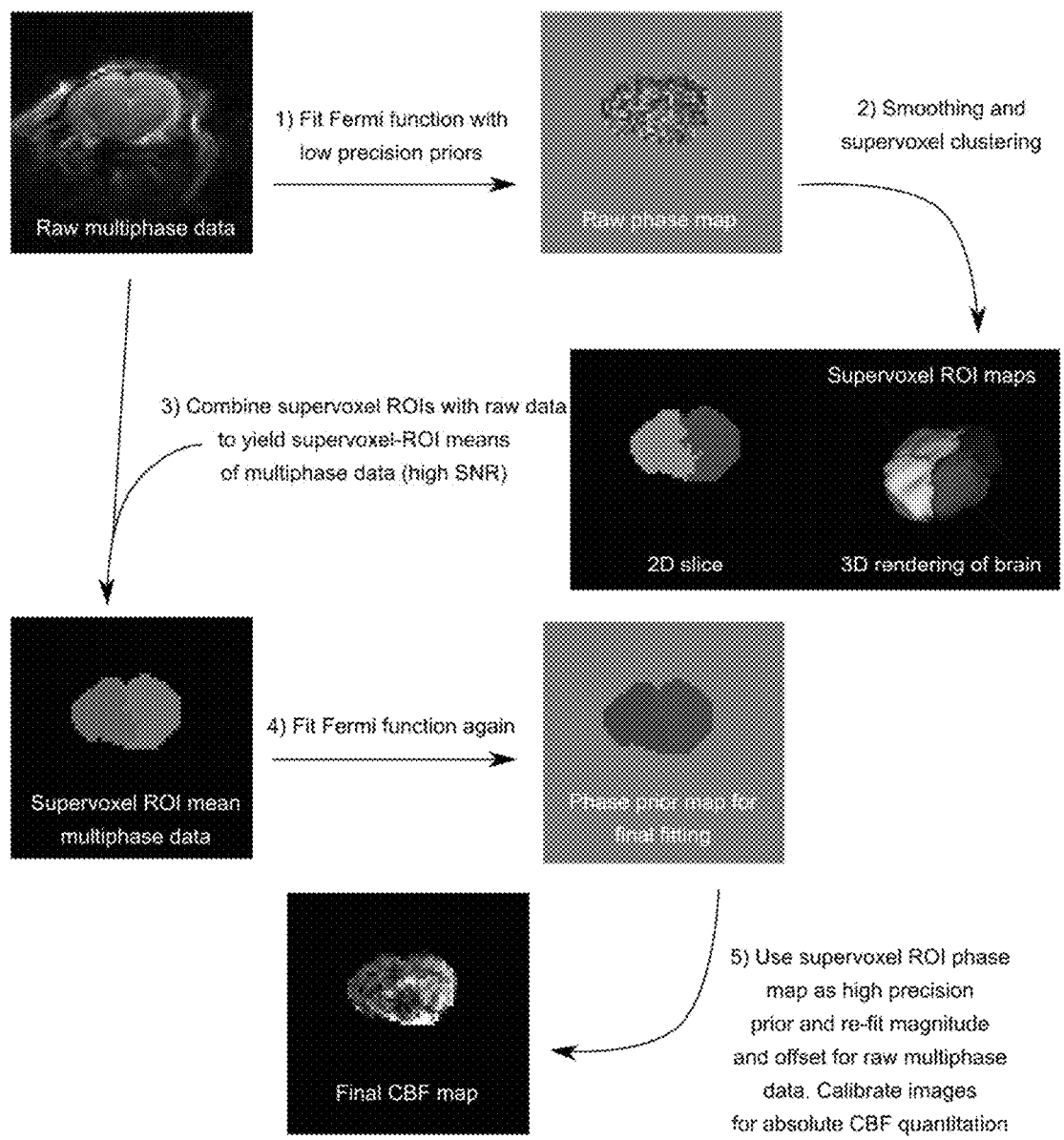
FIG. 9 is a schematic showing the use of clustering of supervoxels in preparing high precision phase map priors.

This dataset was fitted to the Fermi function, estimating a single phase value for each supervoxel ROI. These final phase values were used as a high precision prior for the final fitting of the original raw multiphase data, yielding a voxel-wise map of magnitude and offset. FIG. 9 shows a flow chart of this methodology, including example images derived by the process.

The resultant maps of the magnitude of the fitted function, representing the presence of labelled water in each voxel, were processed with oxford_asl (part of the FMRIB software library [16], [19]) according to the kinetic model of Buxton et al. [20] to produce relative CBF maps. Maps were corrected for coil sensitivity inhomogeneity using the ratio of proton density images acquired with the surface receive array and the volume coil. Final calibration to absolute CBF units was performed using a reference region method. The striatum was chosen as a reference region as the use of CSF, as used in humans, was not practical in rats. The rat striatum is large enough to provide sufficient voxels for analysis, is clearly identifiable, and is easy to use for in vivo $T_1$ and $T_2$ time quantitation whereas rat CSF volume is small and partial volume effects prevent selection of voxels containing CSF alone. A striatum specific tissue:blood partition coefficient for water of 0.97 [21] and inversion efficiencies from simulations for each strain-specific carotid blood velocity (see results) were used. Relaxation parameters for quantitation were blood: $T_1$=2.09±0.02 s, $T_2$=33.2±0.3 ms; reference tissue (striatum): $T_1$=1.47±0.2 s; $T_2$=40.4±8 ms; whole brain: $T_1$=1.6±0.3 s.

For conventional label-control analysis, 0° and 180° images from the multiphase acquisition were used as control and label respectively. CBF quantitation was carried out using the voxel-wise calculation recommended in the White Paper [8]:

$$CBF = \frac{6000 \cdot \lambda \cdot (SI_{control} - SI_{label}) \cdot e^{\frac{PLD}{T_{1,blood}}}}{2 \cdot \alpha \cdot T_{1,blood} \cdot SI_{PD} \cdot \left(1 - e^{-\frac{\tau}{T_{1,blood}}}\right)} \quad \text{(Eq. 4)}$$

where $\lambda$ is the brain/blood partition coefficient of water (0.9 mL/g), $SI_{control}$ and $SI_{label}$ are the signal intensities of the control and label images, PLD is the post label delay (0.55 s), $T_{1,blood}$ is the longitudinal relaxation time of rat arterial blood at 37° C. (2.1 s), a is the labelling efficiency for PCASL (0.85), $SI_{PD}$ is the signal intensity of the proton-density weighted reference image with no labelling pulses, corrected for short TR by multiplying by $(1/(1-e^{-TR/T1,tissue})$ where $T_{1,tissue}$ is the measured longitudinal relaxation time for rat brain (1.6 s), and r is the label duration (1.4 s).

2.6 Autoradiography

CBF was determined using gold standard autoradiography [12], [14] in all three strains (n=3 per strain). Rats were anaesthetised with isoflurane and the femoral artery, vein and a tail vein were cannulated. 4[N-methyl-$^{14}$C] iodoantipyrine (Hartmann Analytic, Germany, specific activity: 55 mCi/mmol) was infused at a linear continuous rate into the femoral vein over 1 minute (50 µCi in 0.5 mL saline). Arterial blood was removed from the animal at the same rate as infusion to maintain a constant blood volume. A pentobarbitone overdose was infused into the tail vein after one minute, followed immediately by decapitation and freezing of the head in isopentane on dry ice. The brain was removed from the frozen head and slices (20 µm thickness) were dried on a hot plate (60° C.) for 10 minutes, exposed to X-ray film with calibrated standard for three days (film: Carestream Kodak BioMax MR; standards: 0-35 µCi/g, ARC; scanner: Expression 10000XL transmittance scanner, Epson, UK). Scanned films were background-subtracted and calibrated against the standards, before conversion to absolute CBF using and the following equation:

$$C_i(T) = \lambda K \int_0^T C_A e^{-K(T-t)} dt \quad \text{(Eq. 5)}$$

where $C_i$ is the concentration of the tracer at final time (T), $\lambda$ is the tissue:blood partition coefficient, $C_A$ is the concentration of the tracer in the artery at time t, and K is a constant that incorporates the rate of blood flow into the tissue (K=mF/Wλ, where m is the diffusion equilibrium between blood and tissue (assumed to be 1) and F/W is the flow of blood per unit mass) [12], [14]. Calibrated images were aligned with respective MRI CBF maps using a manual perspective transform. Whole brain, striatum and cortex ROIs were drawn on the MRI maps and the same ROIs were transferred to the autoradiography images for comparison.

2.7 Statistical Analysis

All results are presented as mean±S.D., unless otherwise specified. Differences between groups were determined using 1-way ANOVA followed, where required, by Tukey's multiple comparison post hoc test. Differences with p<0.05 were considered significant.

3. RESULTS 3.1 Angiography and Labelling Plane Orientation

Figures 2A, 2B:
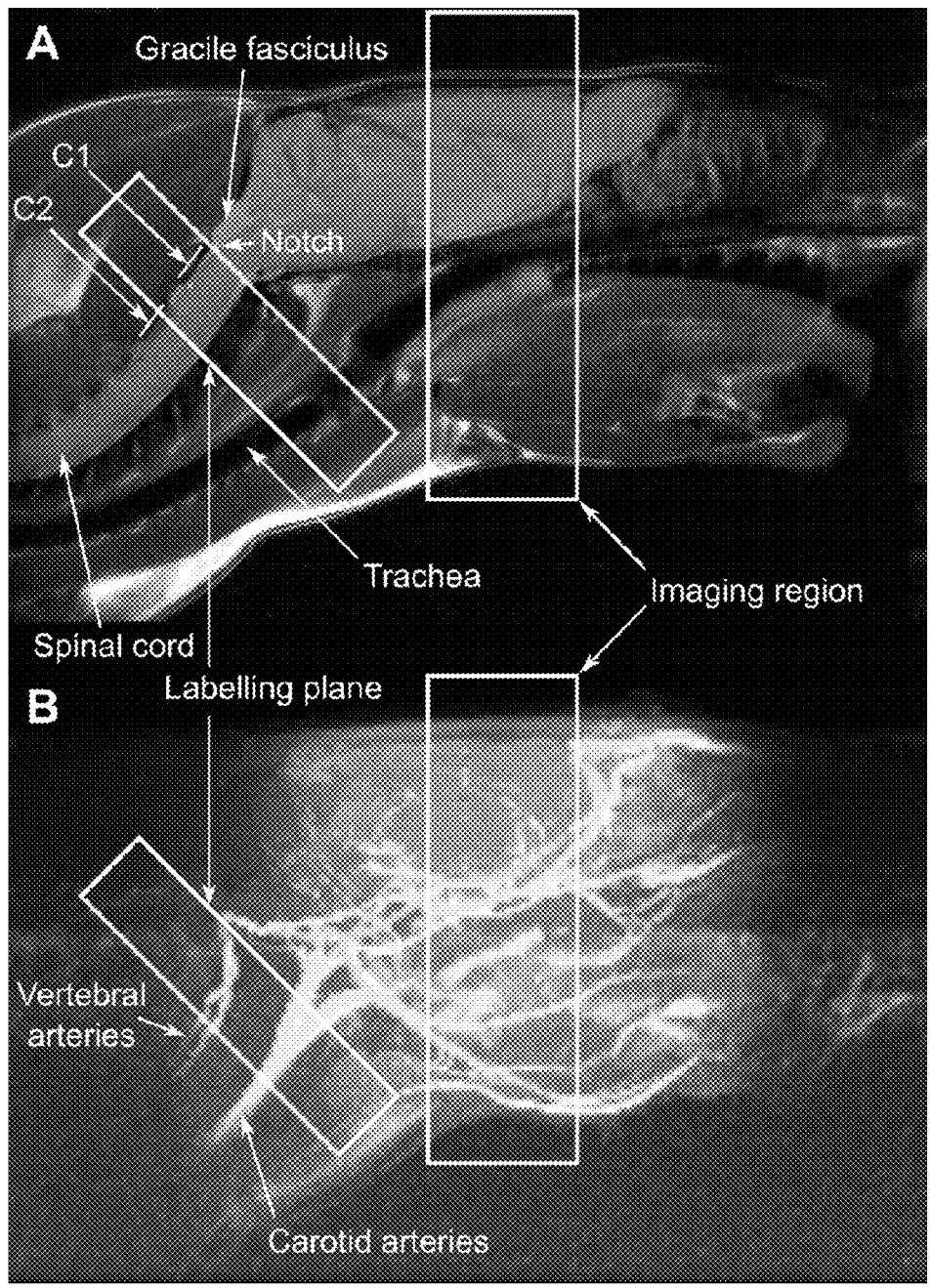
FIG. 2A shows the location of the labelling and imaging regions shown in relation to the brain and the major vessels of the neck, superimposed over an anatomical, fast echo sagittal midline image of a Sprague-Dawley (SD) rat head. Positions of C1 and C2 vertebra are visible and the notch immediately caudal to the gracile fasciculus can be identified.
FIG. 2B shows location of the labelling and imaging regions shown in relation to the brain and the major vessels of the neck, superimposed over a maximum intensity projection of time-of-flight (TOF) angiography with the same field of view as shown in FIG. 2A.

Time-of-flight angiography showed orientation and location of major vessels with respect to head, neck and brain anatomy visible on high-resolution structural images (FIGS. 2A-2B). No discernible differences in relative geometry were evident between strains of rat or between smaller and larger rats (range from 180-340 g). Carotid and vertebral arteries ran angles of 42±7° and 44±8°, respectively, with respect to the longitudinal axis of the rat and in no strain was there a significant difference in angle between the carotid and vertebral arteries (p>0.05). The bend in the vertebral arteries immediately rostral to the C1 vertebra, and just prior to the entrance into the skull, marks the limit of the region where the vessels are straight and parallel. This region can be seen as the notch immediately caudal to the *gracile fasciculus* and is easily visible on sagittal midline anatomical images (FIG. 2A).

Figure 8A:
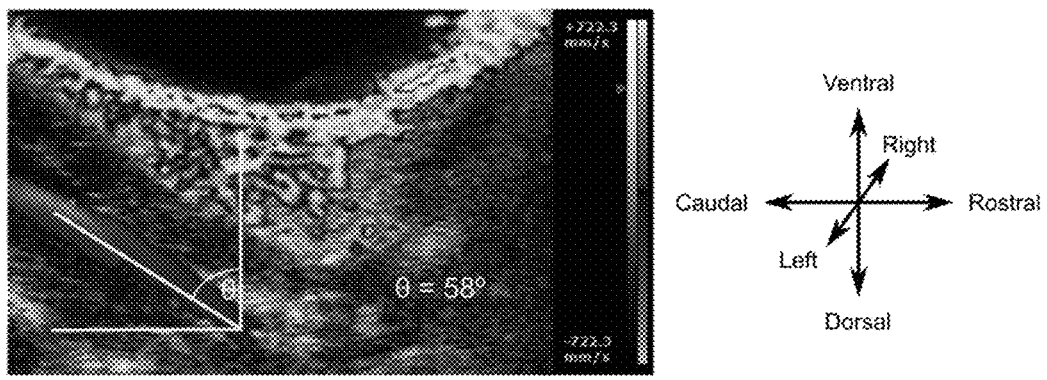
FIG. 8A is an example ultrasound image of a rat neck with the carotid artery in blue indicating blood flowing away from the probe (top left to bottom right in this image).
Figure 8B:
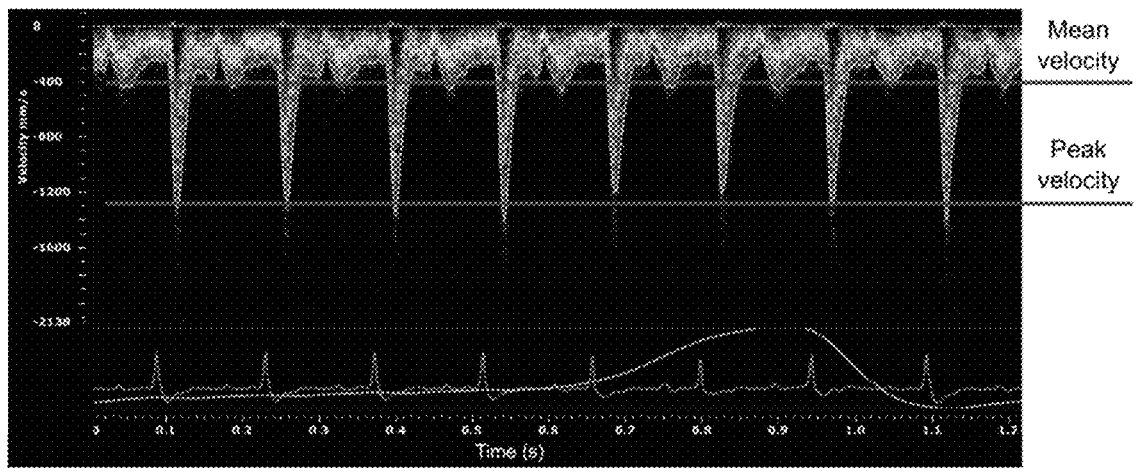
FIG. 8B illustrates a typical trace of blood flow velocity against time in an SD rat with mean and peak velocities indicated.

The orientation of the labelling plane across the neck impacted both absolute CBF quantitation and error in quantitation of the CBF maps. Flow-driven adiabatic inversion is most efficient when the flow of blood is perpendicular to the labelling plane. A labelling plane at 45° with respect to the longitudinal axis of the animal crosses arteries close to perpendicularly. The CBF maps obtained at the 45° labelling angle exhibited lower variance in voxel-wise CBF values (p<0.01; F test) and had more physiologically realistic absolute CBF values than images acquired with a labelling plane 0° (p<0.001; t test; FIG. 8A). Example CBF maps are shown in FIG. 8B.

3.2 Blood Velocity Measurements

Figure 3A:
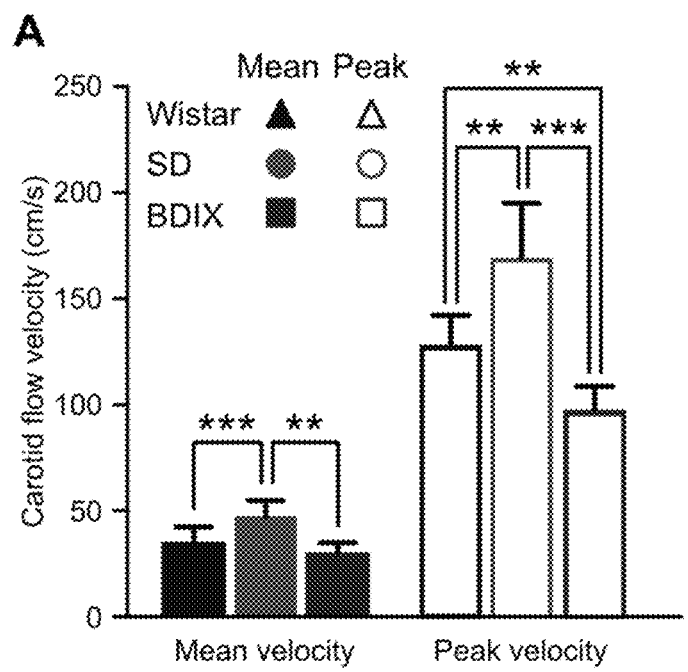
FIG. 3A is a graph showing mean and peak carotid artery flow velocities in three strains of rats: Wistar, SD, and Berlin-Druckrey IX (BDIX).
Figure 3B:
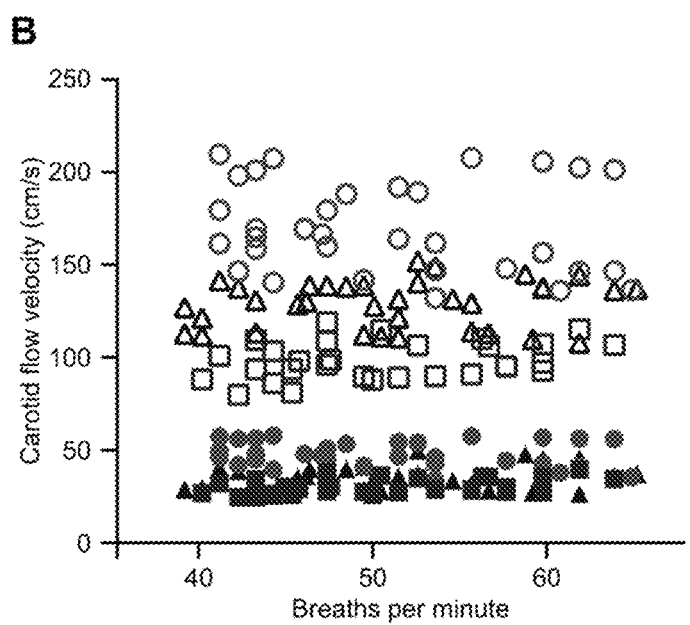
FIG. 3B is a graph showing mean and peak carotid artery flow velocities as a function of anaesthetic depth, as indicated by breathing rate.

Carotid artery blood flow velocities were measured by Doppler ultrasound in Wistar, SD and BDIX rats (n=3 for each strain). Typical acquisition traces and images, from which mean and peak (systolic) flow velocities were determined, are shown in FIGS. 8A-8B. Mean carotid artery flow velocity was significantly higher in SD rats compared to either BDIX or Wistar rats (47±6 cm/s for SD vs 30±10 cm/s for BDIX, p<0.001; and 35±7 cm/s for Wistar, p<0.01; FIG. 3A). Peak carotid artery flow velocity was lowest in BDIX rats (100±30 cm/s), increased in Wistar rats (130±20 cm/s;

p<0.01) and increased again in SD rats (170±20 cm/s; p<0.01). No significant difference was evident in either peak or mean flow velocity as a function of respiration rate within any strain (FIG. 3B).

3.3 Simulation Results

Figure 3C:
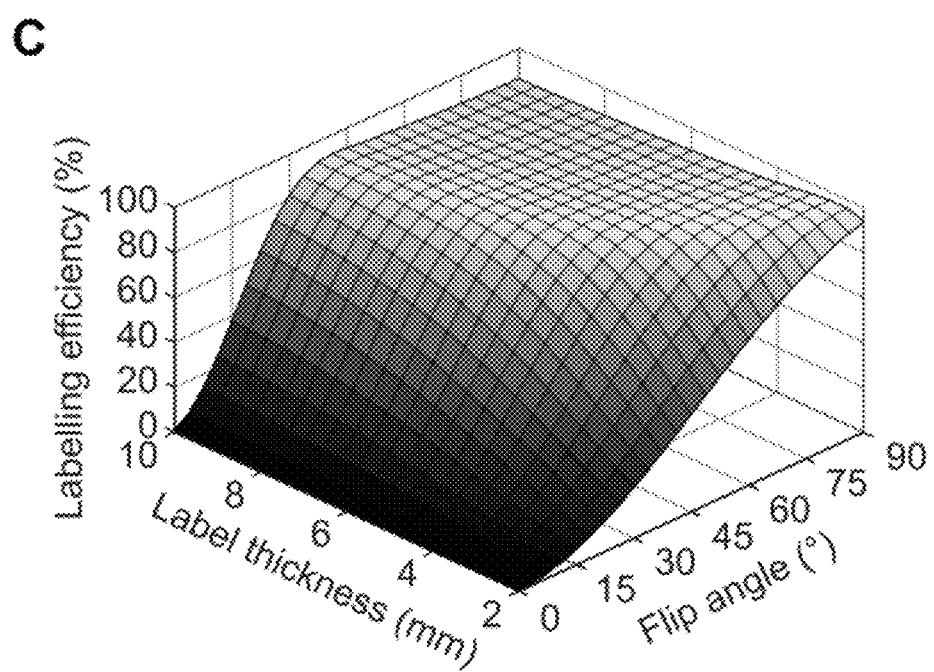
FIG. 3C illustrates Bloch simulation results showing labelling efficiency (inversion achieved as a percentage of theoretical inversion possible), for blood as it passes through labelling planes of 2-10 mm thickness with flip angles in the labelling pulse train between 2° and 90° at 37 cm/s (mean carotid velocity for all rats studied).
Figure 10A:
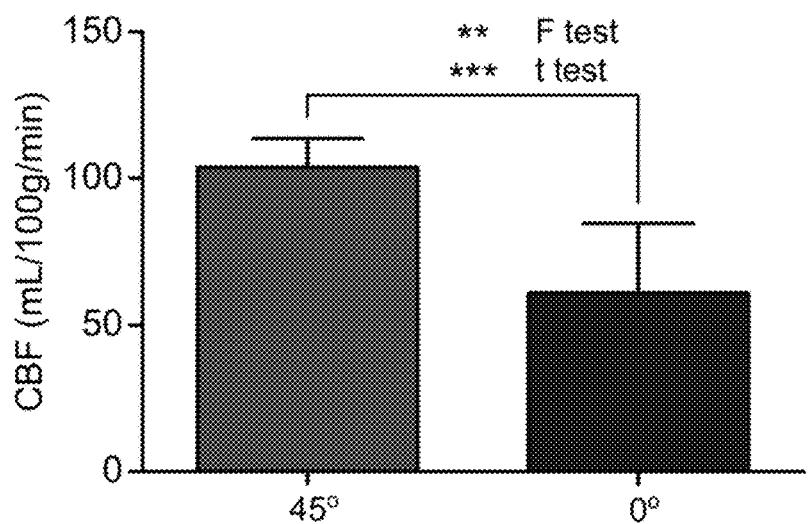
FIG. 10A is a graph representing CBF quantitation with a labelling plane angle of 0° or 45° with respect to the longitudinal axis of the animal (CBF values: t test *p<0.001; variance: F test p<0.01).
Figure 10B:
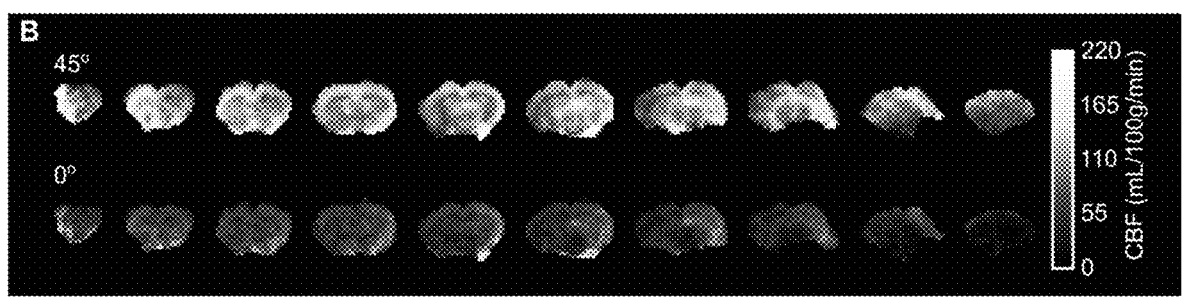
FIG. 10B is an example CBF map acquired with labelling angles of 45° and 0° from a female BDIX rat. All other parameters of acquisition identical. Four averages were acquired per image. Images represent successive coronal sections of the brain from rostral to caudal (left to right in the figure).

Numerical simulations showed that inversion efficiencies diminished dramatically with low flip angles (<30°), especially with narrow labelling planes and/or high blood velocities. However, there exists a plateau of high and relatively uniform inversion efficiency at higher labelling region thicknesses and flip angles (FIG. 3C). A labelling region thickness of 6.2 mm and a flip angle of 40° was selected for in vivo experiments to achieve maximum inversion efficiency across a range of physiologically relevant blood velocities (25-50 cm/s; FIGS. 10A-10B). Simulated inversion efficiencies for strain-specific mean arterial velocities were 85% (Wistar), 75% (SD) and 87% (BDIX).

3.4 Relaxometry Results

Whole, 100% oxygenated, rat blood relaxation times at 37° C. and 9.4 T were: $T_1$=2.09±0.02 s; $T_2$=33.2±0.3 ms. In vivo striatum relaxation times were: $T_1$=1.47±0.2 s; $T_2$=40.4±8 ms. In vivo whole brain $T_1$ time was 1.6±0.3 s (n=21 rats across 3 strains). These values were used to calibrate quantitation procedures as described in the methods.

3.5 Post-Label Delay and Arrival Time

Figure 4A:
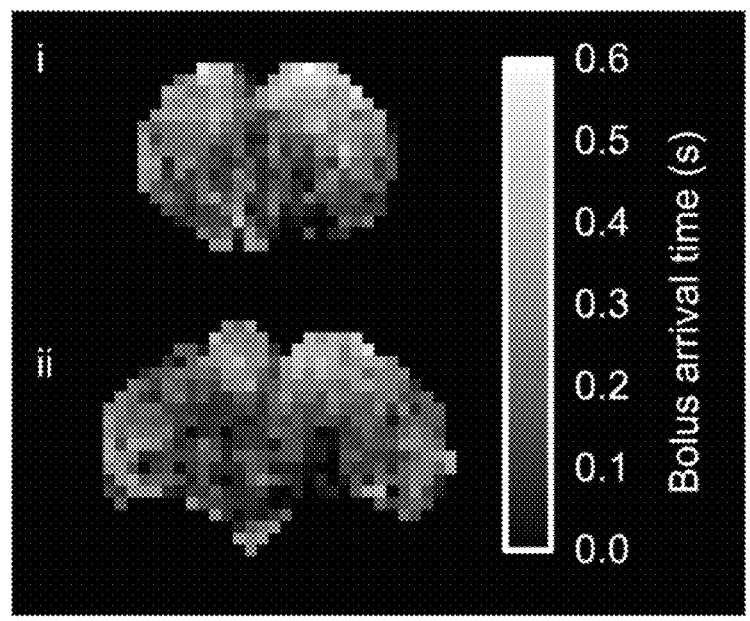
FIG. 4A shows bolus arrival time maps from (i) anterior slice (immediately caudal to the olfactory sulcus), and (ii) posterior slice (10 mm caudal to the anterior slice) from an example BDIX rat brain.
Figure 4B:
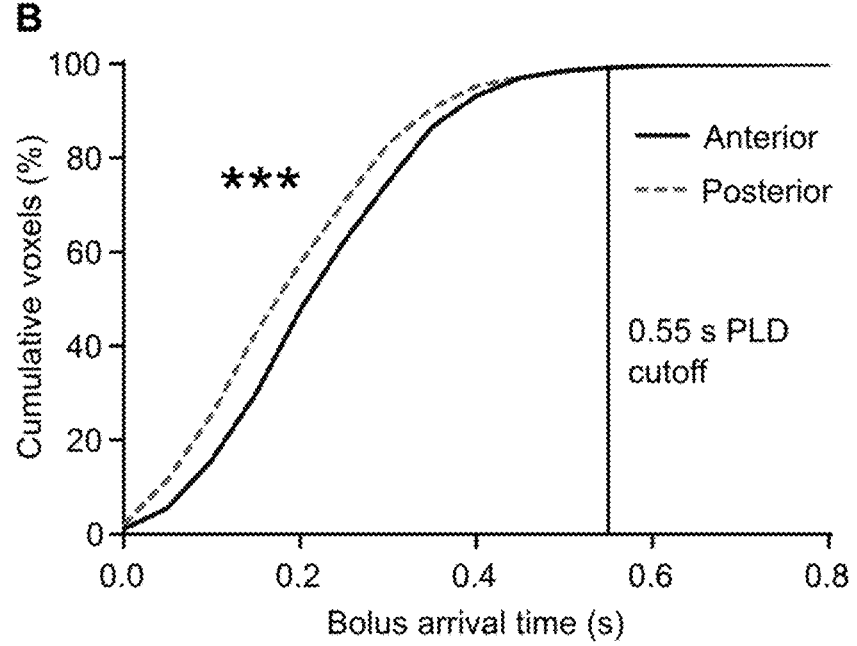
FIG. 4B is a graph showing cumulative frequency distributions of voxel arrival time at the anterior and posterior of rat brains from three strains (n=11; ***p<0.001). The PLD cut-off represents the point at which arterial transit (cumulative voxels) had occurred in 99% of voxels imaged.

Images acquired with varying post-label delays, between 10 and 1000 ms, were used to construct blood bolus arrival time maps (FIG. 4A). Two slices, one at the front and one at the back of the brain, acquired in 50 ms per slice, were used to represent the range of possible arrival times; imaging delays when using larger numbers of slices rendered estimates of arrival time imprecise. As expected, in all strains, blood arrived at the anterior slice later than it arrived at the posterior slice (p<0.001, Kolmogorov-Smirnov test; FIG. 4B), but there was a large overlap between the range of arrival times at the front and back of the brain. A post-label delay of 550 ms was chosen for subsequent imaging in naïve rats as 99% of voxels in both slices had an arrival time shorter than this.

3.6 Labelling Plane Location and Duration

Figure 5A:
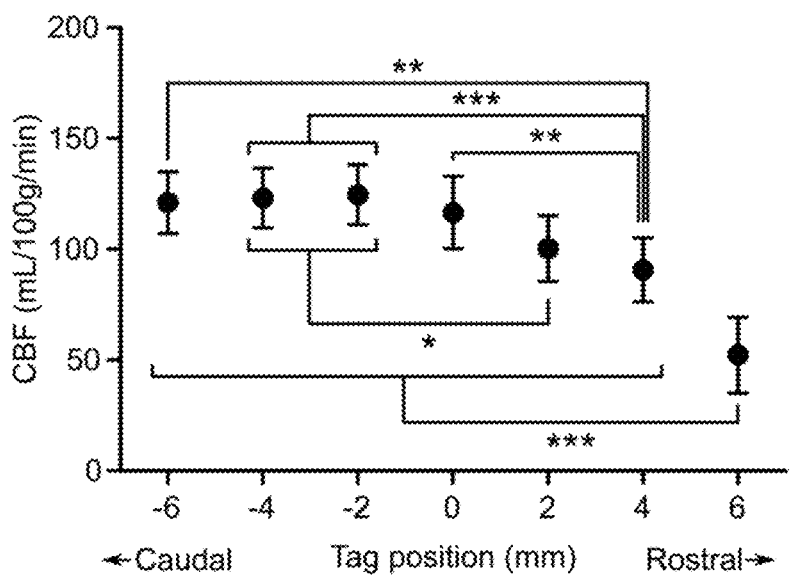
FIG. 5A is a graph showing the effect of labelling plane location on cerebral blood flow (CBF) measurements. Negative label positions are located towards the tail of the animals, positive positions towards the nose. 0 mm is the position of the labelling plane shown in FIGS. 2A-2B, at which the labelling plane is entirely spanning straight and parallel vessels, each passing close to perpendicular through the labelling plane (n=9, across 3 strains; *p<0.001; p<0.01; *p<0.05).
Figure 5B:
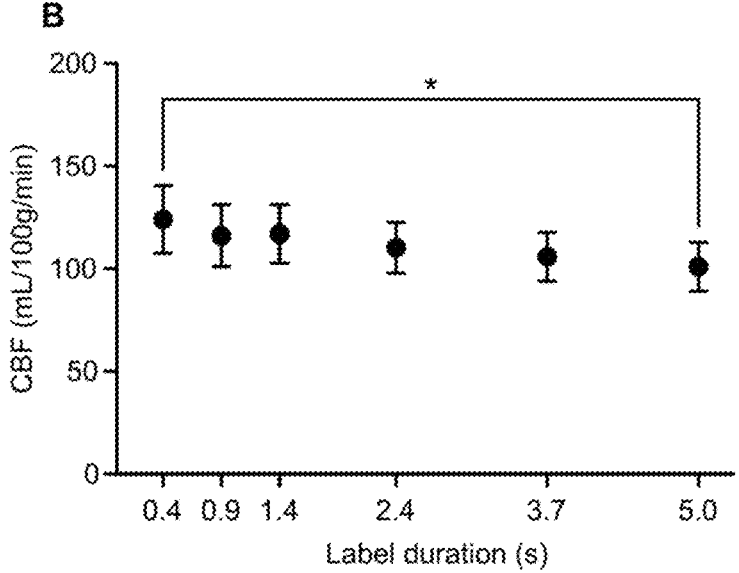
FIG. 5B is a graph illustrating the effect of label duration on CBF measurements (*p<0.05. n=9, across 3 strains).
Figure 11:
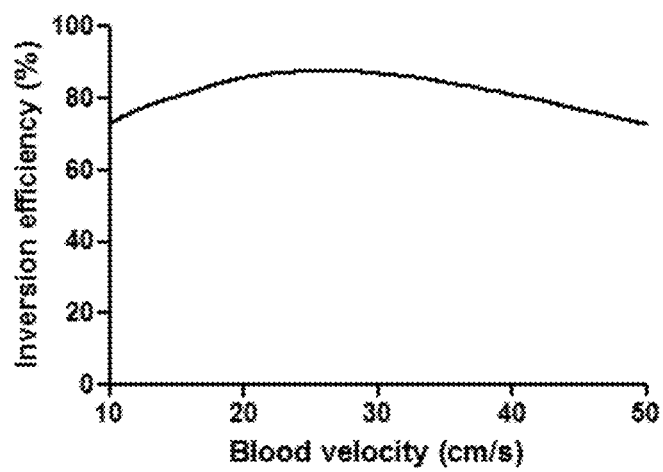
FIG. 11 shows predicted inversion efficiencies at a range of blood flow velocities with a 6.2 mm thick labelling plane and a flip angle of 40°. Other parameters as described in methods section.

The position of the labelling plane was moved along the axis of the vessels in the neck over a range of 12 mm. The extent of this range was ultimately limited by interference with the imaging plane at the rostral end and by efficiency of the labelling coil (volume transmit RF coil was used for labelling pulses) at the caudal end. However, before reaching the rostral limit, the labelling plane moves across regions where the feeding arteries have entered the brain and no longer run perpendicular to the labelling plane, for example as the vertebral arteries enter the skull, blood flows parallel to the labelling plane (FIG. 2B). These imperfections affect labelling efficiency and lead to artificially decreased CBF values (FIG. 5A). When the labelling plane was moved behind this point, where the feeding vessels were straight and parallel, no significant effect on calculated CBF values was found. There was no difference between CBF at any label duration between 0.9 s and 3.7 s. There was a statistically-significant lower CBF with label duration of 5 s than a duration of 0.4 s (124±20 vs. 100±12 mL/100 g/min, p<0.05; FIG. 5B). Longer label durations required longer TR times but were not able to increase ASL signal sufficiently to justify the longer acquisition times. An efficient label duration in terms of ASL signal accumulated as a function of scan time was 1.4 s (FIG. 11).

3.7 Comparison to Autoradiography

Figure 5C:
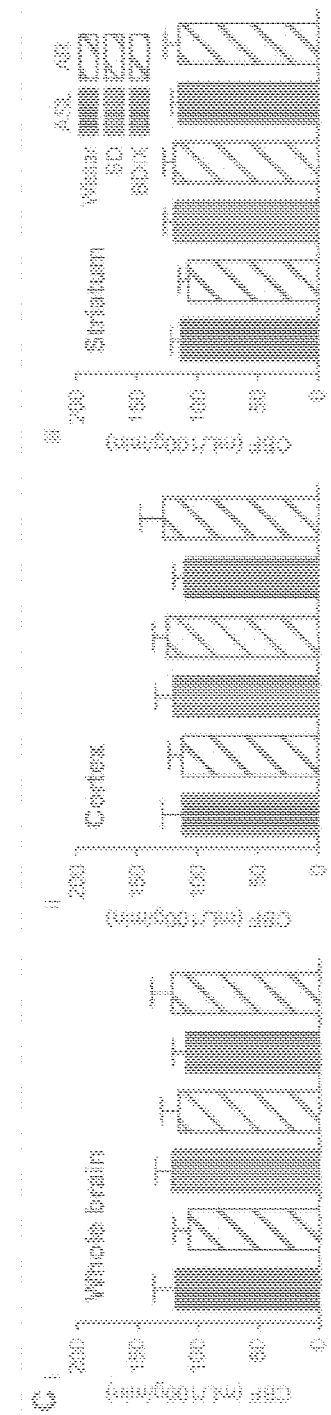
FIG. 5C illustrates comparisons of cerebral blood flow in different anatomical regions of the brain across 3 species of rats between standard methodologies and methods according to the present disclosure. Comparison between autoradiography (AR) and PCASL (1.4 s label duration) derived CBF values from ROIs covering (i) the whole brain, (ii) the cortex or (iii) the striatum is shown.
Figure 5D:
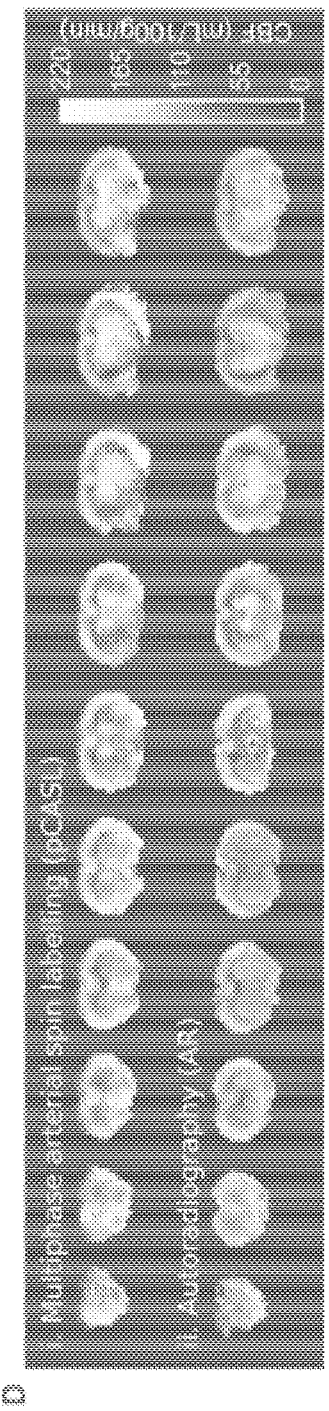
FIG. 5D shows exemplary CBF maps obtained using (i) multiphase PCASL MRI and (ii) autoradiography in a Wistar rat. Images represent successive coronal sections of the brain from rostral to caudal (left to right in the figure).

No significant differences were found in any region (cortex, striatum or whole brain) or strain between CBF values obtained by autoradiography and multiphase PCASL MRI. Representative data acquired with a label duration of 1.4 s is shown in FIG. 5C but there was no difference between PCASL MRI and autoradiography at any tag duration between 0.9 s and 3.7 s (FIG. 5D).

Autoradiography values for whole brain perfusion were 108±12, 116±14 and 122±16 mL/100 g/min in Wistar, SD and BDIX rats, respectively. Multiphase PCASL CBF values across the whole brain in the same animals were 119±17, 122±14 and 110±11 mL/100 g/min, respectively.

3.8 Multiphase Analysis Vs. Label-Control Analysis

Figures 6A, 6B:
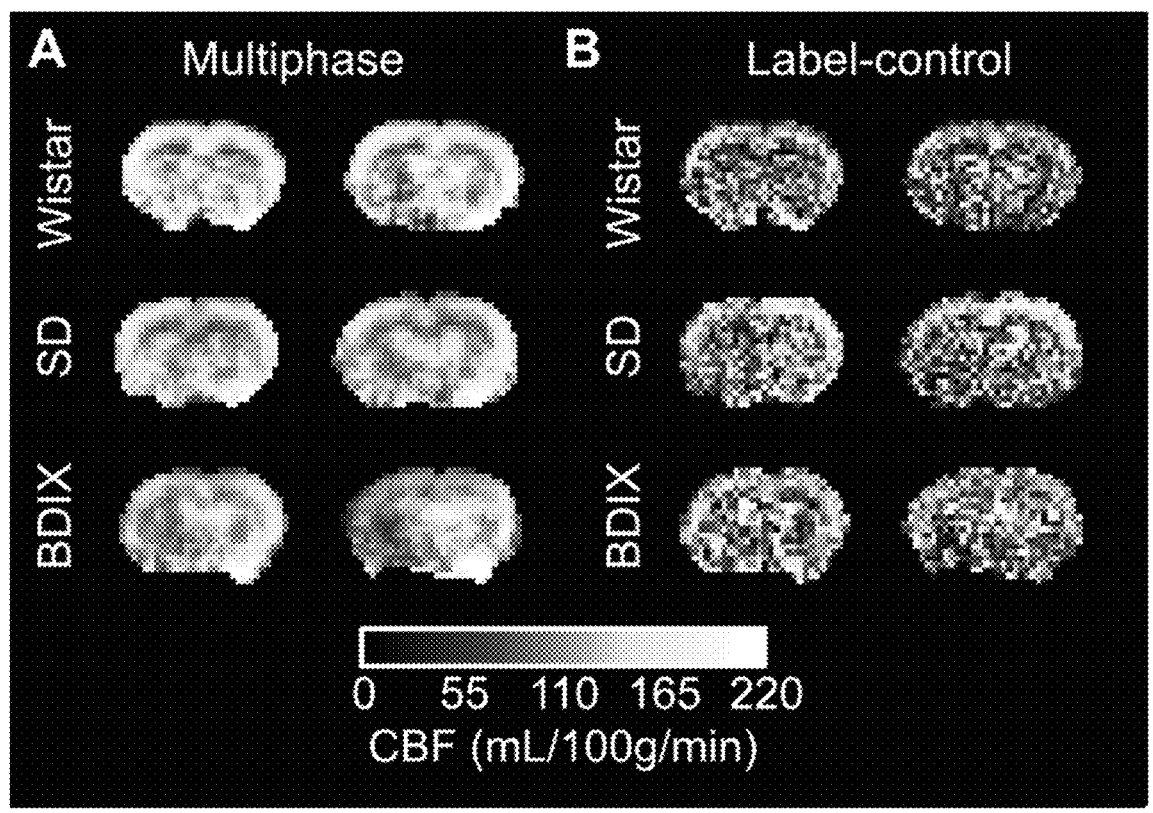
FIGS. 6A-6B illustrate comparative CBF maps in coronal sections of the brain from single-average multiphase PCASL acquisitions (FIG. 6A) and four-average label-control acquisitions in the same animal; total imaging time 89 s (FIG. 6B). Note the lower CBF values, areas of greater heterogeneity and the regions with decreased apparent perfusion in the label-control maps (FIG. 6B).

A comparison between multiphase analysis (FIG. 6A) and the white paper-recommended label-control analysis (FIG. 6B) was made for each animal. Label-control images (effectively 2 phases) can be acquired in one quarter the time of the 8-phase multiphase acquisitions, therefore, four averages were used for the label-control acquisitions for legitimate comparison. Label-control subtractions gave images with lower CBF values (p<0.001) and higher standard deviations (F-test, p<0.01). Additionally, some regions appeared hypoperfused in the label-control images, but multiphase images showed that they were in fact normally perfused. Example maps for each strain are shown in FIGS. 6A and 6B.

3.9 Strain-Specific CBF Measurements

Figure 7A:
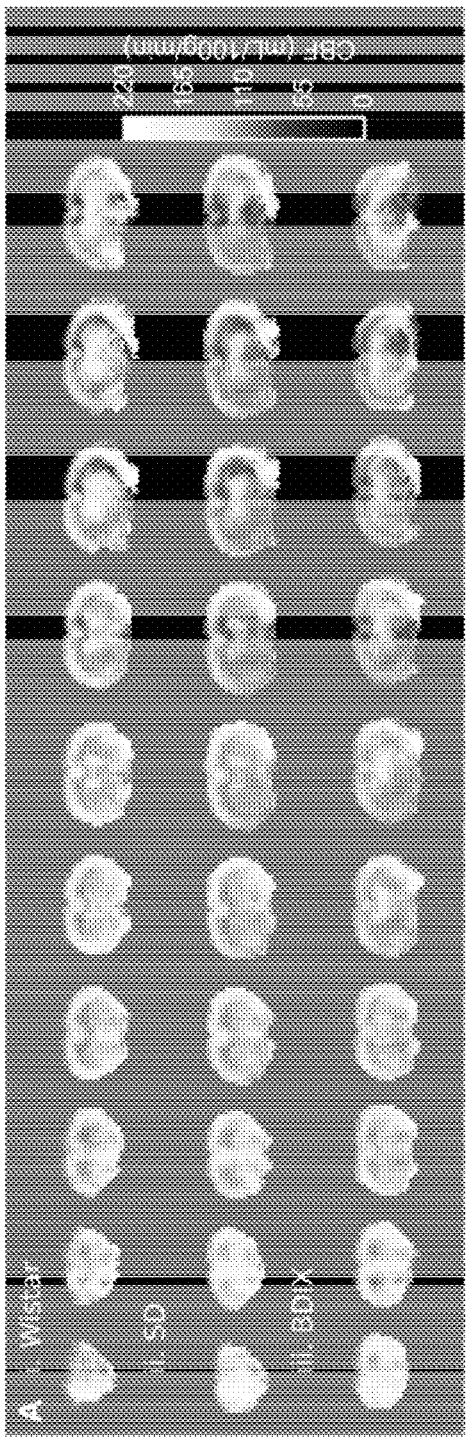
FIG. 7A shows exemplary CBF maps acquired using an embodiment of an optimised multiphase PCASL sequence according to the present disclosure of three strains of rat (Wistar, SD, and BDIX). Eight averages were acquired per image, total imaging time $T_{exp}$=11 m 52 s. Images represent successive coronal sections of the brain from rostral to caudal (left to right in the figure).
Figure 7B:
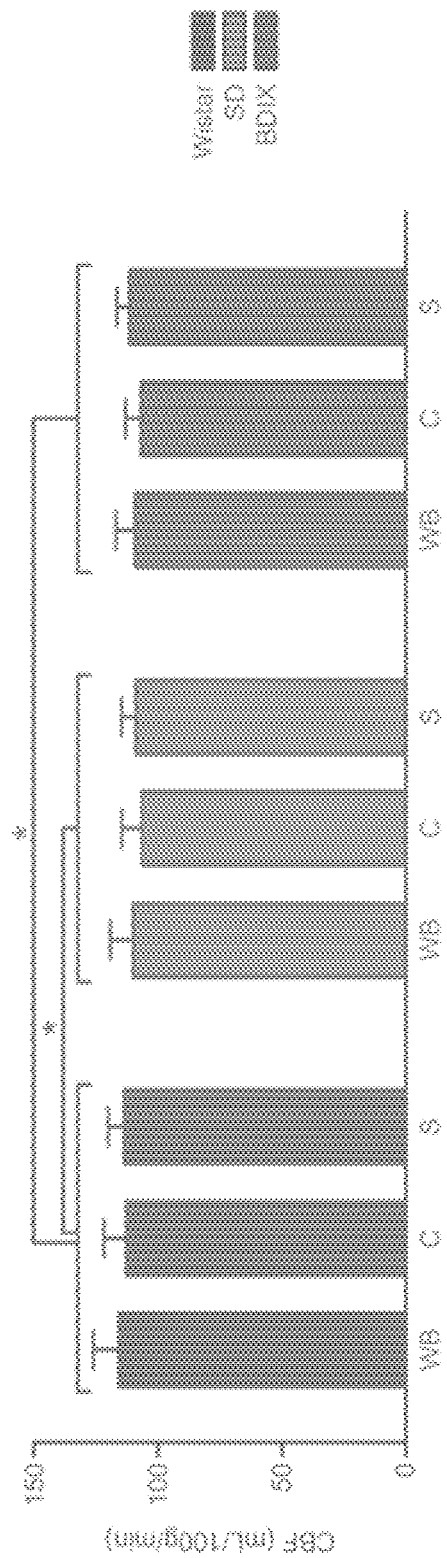
FIG. 7B is a graph representing quantification of CBF mean of whole brain (WB), cortex (C), and striatum (S) in three strains of rats (strains=Wistar, SD, and BDIX; n=7 rats/strain; *p<0.05).

Having validated the optimised multiphase PCASL parameters through comparison of CBF values with gold standard autoradiography, a larger cohort of each strain (n=7 per group, including the 3 autoradiography animals) were subsequently used to assess reproducibility of the multiphase PCASL measurements. Example strain-specific maps of multiphase PCASL CBF values are shown in FIG. 7A. Within each strain, there was no significant difference in CBF between ROIs studied. Whole brain CBF varied very little between strains, being 116±10, 110±9 and 109±8 mL 100 g/min in Wistar, SD and BDIX rats respectively (FIG. 7B). These values show good correspondence with those obtained in the autoradiography experiment with <7% discordance between AR and PCASL CBF values in all strains.

4. DISCUSSION

As described herein, a multiphase PCASL MRI technique was developed and optimised for pre-clinical studies in rats. Imaging parameters better suited for high magnetic field strength imaging in these smaller animals have been discussed above. Choice of imaging parameters was validated by comparison of rat CBF values measured by multiphase PCASL to gold-standard autoradiography in the same animals.

4.1 Validation with gold standard measurements

Autoradiography measurements represent the gold standard in brain perfusion quantification and have a long literature validation behind them [12], [14], [22]. However, they are invasive and terminal procedures, as well as being complex and time consuming to perform and quantify. These factors render autoradiography unsuitable for large numbers of studies, but it remains an excellent calibration point for non-invasive measurements such as PCASL MRI. Here, the autoradiography CBF measurements closely matched those made using multiphase PCASL MRI, thus validating the optimised imaging parameters identified and discussed above.

4.2 Multiphase PCASL Vs. Label-Control ASL

The single largest factor in improving image quality was the implementation and use of the multiphase PCASL technique instead of a simple label-control sequence. In this work, a PCASL implementation was used, which is the clinically recommended method since it does not require continuous radiofrequency (RF) transmitting hardware, and reduces magnetization transfer effects inherently present in the earlier implemented CASL. Moreover, PCASL retains the well-defined bolus duration present in CASL, essential for accurate CBF quantification, whilst maintaining a higher SNR than PASL [8], [23]. Finally, as with CASL, blood labelling occurs in a narrower plane by flow-driven adiabatic inversion. Whilst the multiphase acquisitions can take up to 4 times longer than traditional label-control pairs to acquire, the total imaging time of 89 s for an 8 phase acquisition is not excessive and yields images that show a considerable qualitative and quantitative improvement over acquiring four averages of label-control subtraction in the same time frame. Note also that some regions in the label-control analysis have artificially decreased CBF measurements which affect entire vascular territories. This is a consequence of off-resonance effects affecting one or more vessels running through the labelling plane differently to the other vessels and cannot be corrected for without the multiphase data.

4.3 Labelling Plane Parameters

The ideal labelling plane should be positioned at a point where the traversing arteries are both straight and angled to be approximately perpendicular to the direction of flow in the vessels. If both criteria are met, the exact distance of the labelling plane from the imaging region may be less important. However, for consistency, one location should be chosen for all animals. This point could be determined on an animal-by-animal basis through the use of angiography, but this scan can be avoided through the use of an anatomical reference, as suggested by Alsop and colleagues [8]. Thus, in rodents, data shown and described herein suggest that an optimal positioning can be achieved by placing the labelling plane immediately dorsal to the marked bends in the vertebral arteries, just behind the gracile fasciculus and to the rear of the top of the atlas vertebra (as shown in FIGS. 2A-2B). This is readily identifiable on quick sagittal midline scans and does not vary between rat strains, making it a suitable location.

Figure 12:
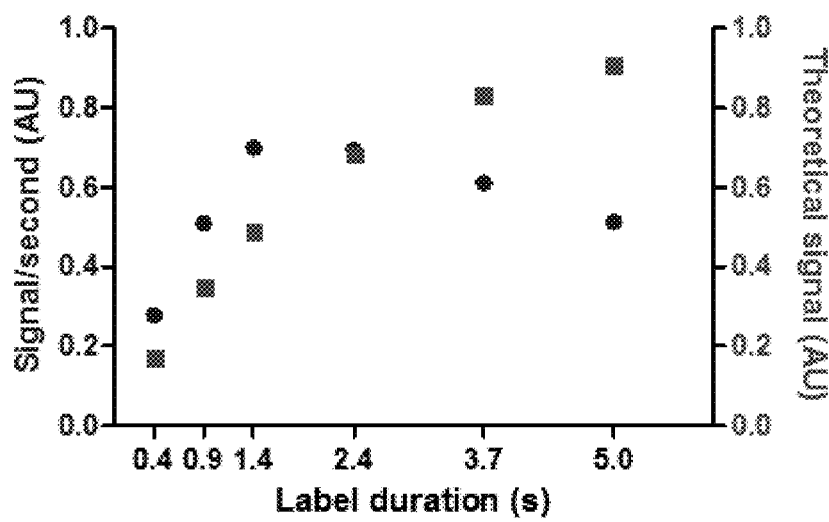
FIG. 12 shows Accumulation of signal (AU) per unit time (i.e. efficiency of imaging) as a function of label duration (blue circles, left axis). Theoretical signal possible with increasing label durations (red squares, right axis).

Corollaries to the position of the labelling plane are its orientation and the label duration. The selection of a 45° labelling plane instead of a 0° plane can decrease error associated with CBF measurements and, importantly, can bring the magnitude of the values closely into alignment with the autoradiography data. With regards to the duration of the labelling period, ASL signal increases as label duration increases, albeit with a plateau at longer labelling times (signal $\propto 1-(e^{-(label\ duration/T_1)})$. However, increasing label duration necessitates increasing TR and thereby increasing the scan time for limited SNR benefit. The efficiency of accumulated signal is similar with tag durations 1.4 s and 2.4 s, the 1.4 s tag duration having a shorter acquisition and therefore offering the better compromise for our purposes (FIG. 12).

An important aspect of the analysis pipeline is the selection of the correct phase priors for model fitting. It is a mathematical problem that three component models which have a phase, amplitude and offset (such as the Fermi function used herein) are prone to overestimation of the amplitude when noise is increased [17]. Noise in the MP PCASL signal may be increased with short label durations as there is less labelled blood in the imaging plane, meaning that changes in image intensity are closer to acquisition and biological noise floors. A consequence of this is that without steps to choose the correct phase for data, the magnitude (and hence CBF) is overestimated (data not shown). By using the supervoxels to cluster phase maps (predominantly within vascular territories in the brain), then averaging the voxels in the original MP PCASL data within each ROI, the SNR of the raw data was increased, at the expense of spatial resolution. This allowed higher precision fitting, yielding higher precision phase values, which in turn yielded more accurate magnitude fitting results. The upshot of this is that the relationship between tag duration and CBF can be broadly flat, without overestimation of CBF at the shorter tag durations. Despite these corrections though, there is still a slight trend for increased measured CBF at the shortest tag durations, which may be an artefact of the very poor ASL data achieved with such short tag durations. In addition, there is a trend for decreased CBF at the longest tag durations. This may be a consequence of inaccurate $T_1$ estimates but is equally likely to be a consequence of not considering outflow of labelled blood from the tissue during the labelling period. In humans, this outflow is considered negligible but in rats, may be a moderate contribution at long labelling times.

4.4 Arrival Time and PLD Selection

A short PLD can be advantageous for maximising the ASL signal as it can minimise $T_1$ recovery of the ASL signal from the labelled water in the imaging region. However, if the PLD is too short, the transit of labelled arterial blood past the imaging region, and into vascular drainage, may be incomplete: this can lead to signal from arterial blood artificially increasing the measured CBF values near arteries and underestimation of tissue CBF elsewhere. As discussed herein, the arterial transit time (ATT) in naïve rats was <550 ms in 99% of voxels, independent of strain. Consequently, a PLD of 550 ms was chosen as the best compromise for maximum signal without arterial contamination. However, in the case of pre-clinical models of brain pathology, particularly where vascular changes are expected to occur, assessment of ATTs in representative animals may be necessary to determine an appropriate PLD for imaging, or multi-PLD protocols could be considered.

4.5 Strain Comparison

Three pre-clinically relevant strains of rats were used herein to assess the reliability of the method across different strains and to determine whether strain specific differences could be observed. Comparing between strains, the Wistar had marginally higher CBF than the SD and BDIX rats. However, a consequence of the differing carotid artery velocities of these strains was that they each had a customised inversion efficiency (broadly similar but ranging from 75% to 87%). If the carotid artery velocities were assumed to be constant between strains, larger and significant differences between strains can emerge—up to 16% difference between strains, vs the 6% with customised inversion efficiencies.

This means that for the most accurate quantitative assessment of CBF in rats, strain-specific carotid velocities may be used to calculate strain-specific inversion efficiencies. However, irrespective of CBF, there was no observable difference in blood arrival time to the brain after the PCASL label meaning that a single PLD may be suitable for all strains of naïve rat.

5. CONCLUSIONS

Optimised parameters for ASL in rats with the aim of improving and standardising quantitative ASL in high magnetic field pre-clinical settings are discussed herein. A multiphase PCASL approach was employed, in which images are acquired at multiple phase angles instead of the traditional label-control (0°-180°) technique, allowing correction for inevitable off-resonance effects and enhancing image quality. An optimal labelling plane position and label parameters for efficient blood inversion have been determined. Suitable labelling durations for maximum efficiency of data accumulation and optimal post-label delay for minimisation of contamination from arterial signal in CBF maps have also been determined. Using gold-standard autoradiography, it was confirmed that optimised multiphase PCASL methods yield accurate CBF values and, thus, provides a rapid and reproducible method for non-invasively measuring CBF in rats.

REFERENCES

[1] D. C. Alsop and J. A. Detre, "Reduced transit-time sensitivity in noninvasive magnetic resonance imaging of human cerebral blood flow," *J Cereb Blood Flow Metab*, vol. 16, no. 6, pp. 1236-1249, November 1996.

[2] J. A. Detre, J. S. Leigh, D. S. Williams, and A. P. Koretsky, "Perfusion imaging," *Magnetic resonance in medicine*, vol. 23, no. 1, pp. 37-45, January 1992.

[3] D. S. Williams, J. A. Detre, J. S. Leigh, and A. P. Koretsky, "Magnetic resonance imaging of perfusion using spin inversion of arterial water," *Proceedings of the National Academy of Sciences of the United States of America*, vol. 89, no. 1, pp. 212-216, January 1992.

[4] Y. Miyaji, M. Yokoyama, Y. Kawabata, H. Joki, Y. Kushi, Y. Yokoi, J. Sasame, S. Seki, K. Mori, T. Kamide, A. Tamase, H. Shima, M. Nomura, Y. Kitamura, and F. Tanaka, "Arterial spin-labeling magnetic resonance imaging for diagnosis of late seizure after stroke.," *Journal of the neurological sciences*, vol. 339, no. 1-2, pp. 87-90, April 2014.

[5] S. Zhang, Y. Yao, S. Zhang, W. Zhu, X. Tang, Y. Qin, L. Zhao, C. Liu, and W. Zhu, "Comparative study of DSC-PWI and 3D-ASL in ischemic stroke patients.," *Journal of Huazhong University of Science and Technology. Medical sciences=Hua zhong ke ji da xue xue bao. Yi xue Ying De wen ban=Huazhong keji daxue xuebao. Yixue Yingdewen ban*, vol. 35, no. 6, pp. 923-927, December 2015.

[6] A. C. Silva, S. G. Kim, and M. Garwood, "Imaging blood flow in brain tumors using arterial spin labeling.," *Magn Reson Med*, vol. 44, no. 2, pp. 169-173, August 2000.

[7] X. J. Qiao, B. M. Ellingson, H. J. Kim, D. J. J. Wang, N. Salamon, M. Linetsky, A. R. Sepandari, B. Jiang, J. J. Tian, S. R. Esswein, T. F. Cloughesy, A. Lai, L. Nghiemphu, and W. B. Pope, "Arterial spin-labeling perfusion MRI stratifies progression-free survival and correlates with epidermal growth factor receptor status in glioblastoma.," *AJNR. American journal of neuroradiology*, vol. 36, no. 4, pp. 672-677, April 2015.

[8] D. C. Alsop, J. A. Detre, X. Golay, M. Gunther, J. Hendrikse, L. Hernandez-Garcia, H. Lu, B. J. Macintosh, L. M. Parkes, M. Smits, M. J. P. van Osch, D. J. J. Wang, E. C. Wong, and G. Zaharchuk, "Recommended implementation of arterial spin-labeled perfusion MRI for clinical applications: A consensus of the ISMRM perfusion study group and the European consortium for ASL in dementia.," *Magn Reson Med*, April 2014.

[9] Y. Gao, C. L. Goodnough, B. O. Erokwu, G. W. Farr, R. Darrah, L. Lu, K. M. Dell, X. Yu, and C. A. Flask, "Arterial spin labeling-fast imaging with steady-state free precession (ASL-FISP): a rapid and quantitative perfusion technique for high-field MRI.," *NMR Biomed*, June 2014.

[10] D. L. Thomas, M. F. Lythgoe, L. van der Weerd, R. J. Ordidge, and D. G. Gadian, "Regional variation of cerebral blood flow and arterial transit time in the normal and hypoperfused rat brain measured using continuous arterial spin labeling MRI.," *J Cereb Blood Flow Metab*, vol. 26, no. 2, pp. 274-282, February 2006.

[11] H. L, U. I, W. J M, and B. E L, "3-Dimensional cerebral blood flow and transit time mouse brain mapping using Dynamic Arterial Spin Labeling," *Proc. Into. Soc. Magn. Reson. Med.*, 2017.

[12] O. Sakurada, C. Kennedy, J. Jehle, J. D. Brown, G. L. Carbin, and L. Sokoloff, "Measurement of local cerebral blood flow with iodo [14C] antipyrine.," *Am J Physiol*, vol. 234, no. 1, pp. H59-H66, January 1978.

[13] Y. Jung, E. C. Wong, and T. T. Liu, "Multiphase pseudocontinuous arterial spin labeling (MP-PCASL) for robust quantification of cerebral blood flow.," *Magn Reson Med*, vol. 64, no. 3, pp. 799-810, September 2010.

[14] M. Reivich, J. Jehle, L. Sokoloff, and S. S. Kety, "Measurement of regional cerebral blood flow with antipyrine-14C in awake cats.," *J Appl Physiol*, vol. 27, no. 2, pp. 296-300, August 1969.

[15] T. W. Okell, M. A. Chappell, M. W. Woolrich, M. Gunther, D. A. Feinberg, and P. Jezzard, "Vessel-encoded dynamic magnetic resonance angiography using arterial spin labeling.," *Magnetic resonance in medicine*, vol. 64, no. 3, pp. 698-706, September 2010.

[16] M. A. Chappell, A. R. Groves, B. Whitcher, and M. W. Woolrich, "Variational Bayesian Inference for a Nonlinear Forward Model," *IEEE Trans. Signal Process.*, vol. 57, no. 1, pp. 223-236, January 2009.

[17] F. C. Alegria, "Bias of amplitude estimation using three-parameter sine fitting in the presence of additive noise," *Measurement*, vol. 42, no. 5, pp. 748-756, 2009.

[18] B. Irving, I. A. Popescu, R. Bates, P. D. Allen, A. L. Gomes, P. Kannan, P. Kinchesh, S. Gilchrist, V. Kersemans, S. Smart, J. A. Schnabel, S. J. M. Brady, and M. A. Chappell, "maskSLIC: Regional Superpixel Generation with Application to Local Pathology Characterisation in Medical Images," *CoRR*, 2016.

[19] A. R. Groves, M. A. Chappell, and M. W. Woolrich, "Combined spatial and non-spatial prior for inference on MRI time-series.," *NeuroImage*, vol. 45, no. 3, pp. 795-809, April 2009.

[20] R. B. Buxton, L. R. Frank, E. C. Wong, B. Siewert, S. Warach, and R. R. Edelman, "A general kinetic model for quantitative perfusion imaging with arterial spin labeling.," *Magn Reson Med*, vol. 40, no. 3, pp. 383-396, September 1998.

[21] C. Leithner, S. Müller, M. Füchtemeier, U. Lindauer, U. Dirnagl, and G. Royl, "Determination of the brain-blood partition coefficient for water in mice using MRI.," *Journal of cerebral blood flow and metabolism: official journal of the International Society of Cerebral Blood Flow and Metabolism*, vol. 30, no. 11, pp. 1821-1824, November 2010.

[22] J. R. Ewing, L. Wei, R. A. Knight, S. Pawa, T. N. Nagaraja, T. Brusca, G. W. Divine, and J. D. Fenstermacher, "Direct comparison of local cerebral blood flow rates measured by MRI arterial spin-tagging and quantitative autoradiography in a rat model of experimental cerebral ischemia.," *J Cereb Blood Flow Metab*, vol. 23, no. 2, pp. 198-209, February 2003.

[23] J. M. Pollock, H. Tan, R. A. Kraft, C. T. Whitlow, J. H. Burdette, and J. A. Maldjian, "Arterial spin-labeled MR perfusion imaging: clinical applications.," *Magnetic resonance imaging clinics of North America*, vol. 17, no. 2, pp. 315-338, May 2009.

[24] J. Risberg and P. Smith, "Prediction of hemispheric blood flow from carotid velocity measurements. A study with the Doppler and 133Xe inhalation techniques.," *Stroke*, vol. 11, no. 4, pp. 399-402, 1980.

[25] J. F. Soustiel, T. C. Glenn, P. Vespa, B. Rinsky, C. Hanuscin, and N. A. Martin, "Assessment of cerebral blood flow by means of blood-flow-volume measurement in the internal carotid artery: comparative study with a 133xenon clearance technique.," *Stroke*, vol. 34, no. 8, pp. 1876-1880, August 2003.

Ratios, concentrations, amounts, and other numerical data may be expressed in a range format. It is to be understood that such a range format is used for convenience and brevity, and should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1% to about 5%, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figure of the numerical value. In addition, the phrase "about 'x' to 'y'" includes "about 'x' to about 'y'".

It should be emphasized that the above-described embodiments are merely examples of possible implementations. Many variations and modifications may be made to the above-described embodiments without departing from the principles of the present disclosure. All such modifications and variations are intended to be included herein within the scope of this disclosure and protected by the following claims.

Therefore, the following is claimed:

1. A computer implemented method for perfusion imaging, comprising:
    positioning a subject in relation to an imaging scanner;
    setting a labeling plane within the subject in which the scanner labels blood;
    labeling blood of the subject in the labeling plane with the scanner with arterial spin labeling using a plurality of phase increments;
    acquiring a data set from the labeled blood in the subject using the imaging scanner;
    reconstructing raw multiphase data from the acquired data set;
    fitting a function to the raw multiphase data to generate a raw parameter map;
    smoothing and clustering the raw parameter map to create clustered region of interest (ROI) maps;
    combining the clustered ROI maps with the raw multiphase data to generate clustered ROI mean multiphase data;
    fitting the clustered ROI mean multiphase data to the function to create parameter prior maps;
    using the parameter prior maps and the clustered ROI maps as a prior to determine a difference in a parameter offset thereof, and using the difference in the parameter offset for re-fitting magnitude and signal offset for the raw multiphase data to generate preliminary blood flow maps;
    calibrating the preliminary blood flow maps for absolute blood flow quantification; and
    generating and outputting final blood flow map images.

2. The method of claim 1, wherein the imaging scanner is a magnetic resonance scanner with a field strength of about 1.2 T, 3 T, 7 T, or 9.4 T.

3. The method of claim 1, wherein a parameter of the raw parameter map is phase or flow velocity.

4. The method of claim 1, wherein the clustering includes a grouping of regions of voxels having a commonality of phase parameters, flow velocity parameters, or both.

5. The method of claim 1, wherein the labeling plane is in the neck of the subject, offset with respect to the longitudinal axis of the subject by an offset angle and about perpendicular to one or more carotid arteries of the subject.

6. The method of claim 1, wherein the plurality of phase increments are separated by a phase angle of about 0 to about 180.

7. The method of claim 1, wherein the clustering is voxel, supervoxel clustering, or k-means clustering.

8. The method of claim 1, wherein the function is a fermi function or a modified fermi function.

9. The method of claim 1, further comprising processing the final blood flow maps with post-hoc spatial smoothing or spatial regularization, individually or in combination.

10. The method of claim 1, wherein the final blood flow maps are maps of cerebral blood flow.

11. The method of claim 1, wherein the parameter offset is a phase offset.

12. A computer implemented method for perfusion imaging, comprising:
    positioning a subject in relation to an imaging scanner;
    setting a labeling plane within the subject in which the scanner labels blood;
    labeling blood in an area of the subject in the labeling plane using a plurality of phase increments and an imaging scanner;
    acquiring a data set from the labeled blood in the subject using the imaging scanner;
    reconstructing raw multiphase data from the acquired data set;
    fitting the raw multiphase data to a function;
    averaging the fitted data;
    combining the averaged fitted data with the raw multiphase data;
    fitting the combined data to the function and correcting for parameter offsets to generate preliminary blood flow maps;
    calibrating the fitted corrected combined data for absolute blood flow quantification; and
    generating and outputting final blood flow maps, wherein the final blood flow maps comprise quantitative blood flow information.

13. The method of claim 12, wherein the blood is labeled in a labeling plane relative to the subject about 0 to about 180 degrees offset from a longitudinal axis of the subject.

14. The method of claim 12, wherein the blood is labeled in a labeling plane that is about perpendicular to one or more carotid arteries of the subject.

15. The method of claim 12, wherein the plurality of phase increments are separated from each other by a phase angle of about 0 to about 180 degrees.

16. The method of claim 12, wherein the function is a Fermi function, modified Fermi function, or a sinusoidal function.

17. The method of claim 12, wherein the averaging is performed with supervoxel clustering or k-means clustering.

18. The method of claim 12, further comprising post-processing the final blood flow maps with post-hoc spatial smoothing or spatial regularization, individually or in combination.

19. The method of claim 12 wherein the parameter offsets are phase offsets.

20. A system, comprising:
a magnetic resonance (MR) imaging scanner;
at least one computing device having a processor and a memory; and
at least one application executable in the at least one computing device stored in the memory that, upon positioning a subject in relation to the imaging scanner and setting a labeling plane within the subject in which the scanner labels blood, when executed by the processor, the application causes the computing device to at least:
label blood in an area of the subject in the labeling plane using a plurality of phase increments and the imaging scanner;
acquire a multiphase data set from the labeled blood in the subject using the imaging scanner;
reconstruct raw multiphase data from the acquired data set;
fit the raw multiphase data to a function;
average the fitted data;
combine the averaged fitted data with the raw multiphase data;
fit the combined data to the function and correct for phase offsets to generate preliminary blood flow maps;
calibrate the corrected fitted combined data for absolute blood flow quantification; and
generate and output final blood flow maps, wherein the final blood flow maps comprise quantitative blood flow information.

21. A system, comprising:
a magnetic resonance (MR) imaging scanner;
at least one computing device having a processor and a memory; and
at least one application executable in the at least one computing device stored in the memory that, upon positioning a subject in relation to the imaging scanner and setting a labeling plane within the subject in which the scanner labels blood, when executed by the processor, the application causes the computing device to at least:
label blood of the subject in the labeling plane with the imaging scanner with arterial spin labeling using a plurality of phase increments;
acquire a data set from the labeled blood in the subject using the imaging scanner;
reconstruct raw multiphase data from the acquired data set;
fit a function to the raw multiphase data to generate a raw parameter map;
smooth and cluster the raw parameter map to create one or more clustered region of interest (ROI) maps;
combine the one or more clustered ROI maps with the raw multiphase data to generate clustered ROI mean multiphase data;
fit the clustered ROI mean multiphase data to the function to create parameter prior maps;
use the parameter prior maps and the one or more clustered ROI maps as a prior to determine a difference in the parameter offset thereof, and use the difference in the parameter offset for re-fitting magnitude and signal offset for the raw multiphase data to generate preliminary blood flow maps;
calibrate the preliminary blood flow maps for absolute blood flow quantification; and
generate and output final blood flow map images.

* * * * *